US006690467B1

(12) United States Patent
Reel

(10) Patent No.: US 6,690,467 B1
(45) Date of Patent: Feb. 10, 2004

(54) OPTICAL SYSTEM AND METHOD FOR OPTICALLY ANALYZING LIGHT FROM A SAMPLE

(75) Inventor: Richard T. Reel, Hayward, CA (US)

(73) Assignee: PE Corporation, Foster City, CA (US)

( * ) Notice: Subject to any disclaimer, the term of this patent is extended or adjusted under 35 U.S.C. 154(b) by 0 days.

(21) Appl. No.: 09/564,790

(22) Filed: May 5, 2000

(51) Int. Cl.[7] .................................................. G01J 3/28
(52) U.S. Cl. ........................ 356/328; 359/642; 359/656
(58) Field of Search ................................ 356/326, 344, 356/328, 330, 432; 359/642, 656, 649

(56) References Cited

U.S. PATENT DOCUMENTS

| | | |
|---|---|---|
| 2,847,899 A | 8/1958 | Walsh |
| 3,247,758 A | 4/1966 | Turner |
| 3,752,585 A | 8/1973 | Elliott |
| 3,837,744 A | 9/1974 | Egan et al. |
| 4,017,185 A | 4/1977 | Chupp |
| 4,049,353 A | 9/1977 | Missio |
| 4,289,401 A | 9/1981 | Mohr |
| 4,462,687 A | 7/1984 | Krause |
| 4,714,345 A | 12/1987 | Schrader |
| 4,919,537 A | 4/1990 | Giebeler |
| 5,091,652 A | 2/1992 | Mathies et al. |
| 5,206,701 A | 4/1993 | Taylor et al. |
| 5,260,767 A | 11/1993 | Cook |
| 5,268,080 A | 12/1993 | Kambara et al. |
| 5,329,353 A | 7/1994 | Ichimura et al. |
| 5,372,783 A | 12/1994 | Lackie |
| 5,442,440 A | 8/1995 | Harada |
| 5,445,934 A | 8/1995 | Fodor et al. |
| 5,498,324 A * | 3/1996 | Yeung et al. ................ 204/452 |
| 5,559,597 A | 9/1996 | Battey et al. |
| 5,638,173 A | 6/1997 | Smith et al. |
| 5,644,396 A | 7/1997 | Hopkins, II |
| 5,742,389 A | 4/1998 | Zavislan et al. |
| 5,880,832 A | 3/1999 | Eastman et al. |
| 5,938,908 A | 8/1999 | Anazawa et al. |
| 5,949,532 A | 9/1999 | Schrof et al. |
| 5,949,541 A | 9/1999 | Merle |
| 6,017,434 A * | 1/2000 | Simpson et al. ............ 204/612 |
| 6,038,023 A | 3/2000 | Carlson et al. |
| 6,103,083 A * | 8/2000 | Merenkova et al. ........ 204/603 |

FOREIGN PATENT DOCUMENTS

| | | |
|---|---|---|
| DE | 34 03 372 C1 | 7/1985 |
| EP | 0 294 524 A1 | 12/1988 |
| EP | 543 578 B1 | 6/1995 |
| WO | WO 97/36681 | 10/1997 |

OTHER PUBLICATIONS

Reel, Richard T., Apr. 23, 1997, "Camera Lens Spectrograph Optics Designed for MegaGUT," from http://www.best.com/~rcuria/report/m_optics.html, printed Mar. 28, 2000.

United States Statutory Invention Registration No. H1152, C. Korendyke, Imaging Channeled Spectrography, published Mar. 2, 1993.

* cited by examiner

Primary Examiner—Frank G. Font
Assistant Examiner—Roy M Punnoose
(74) Attorney, Agent, or Firm—Finnegan, Henderson, Farabow, Garrett & Dunner, L.L.P.

(57) ABSTRACT

An optical system for analyzing light from a plurality of samples is provided. The optical system includes a plurality of holders adapted to have samples located therein, a collection lens, a transmission grating, and a reimaging lens. The collection lens is configured to receive and substantially collimate light from the samples. The transmission grating is configured to spectrally disperse the substantially collimated light from the collection lens. The reimaging lens is configured to receive the light from the light dispersing element and direct the light onto a light detection device. A method of optically analyzing at least one sample is also provided.

191 Claims, 14 Drawing Sheets

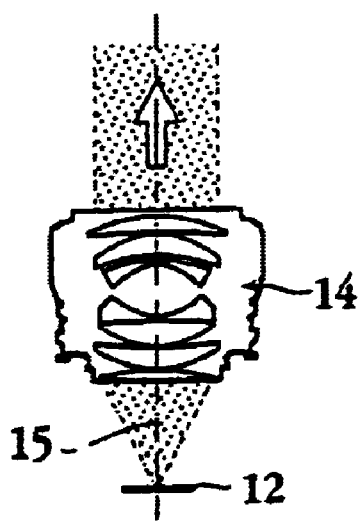
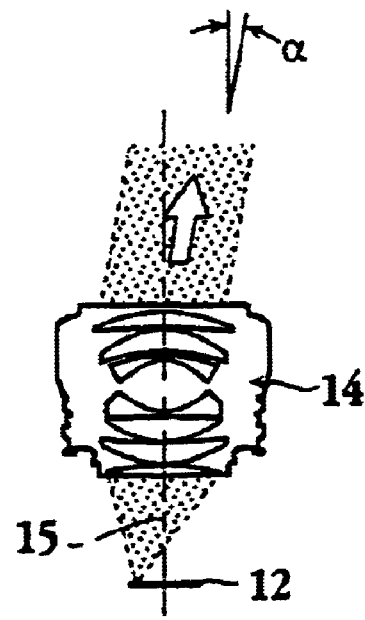
Fig. 5A     Fig. 5B
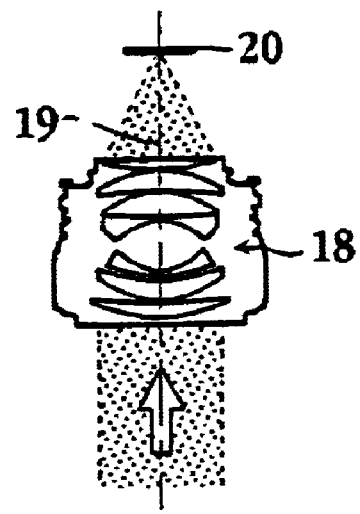
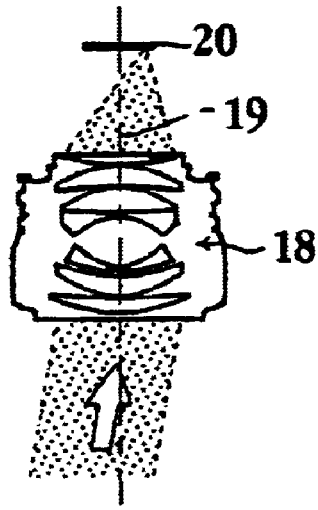
Fig. 6A     Fig. 6B

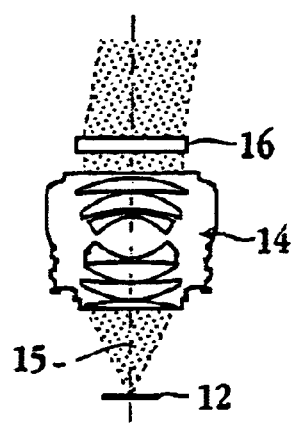 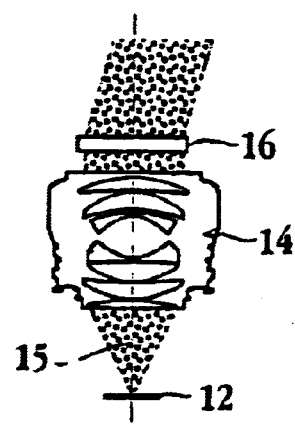
Fig. 7A    Fig. 7B
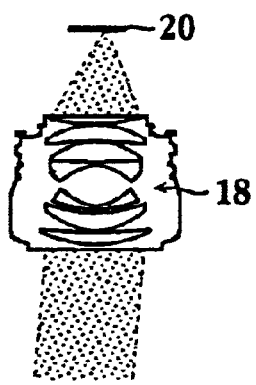 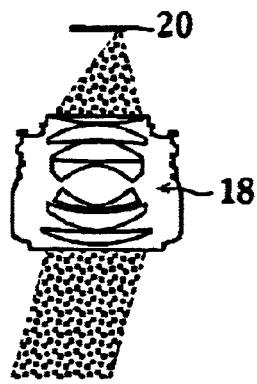
Fig. 8A    Fig. 8B
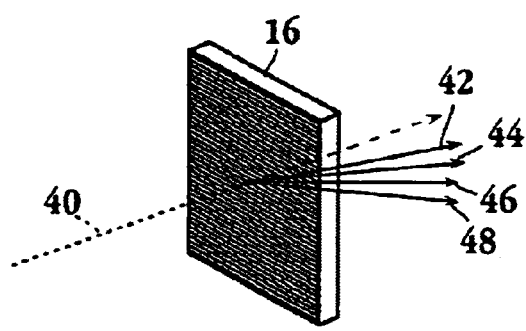
Fig. 9

US 6,690,467 B1

OPTICAL SYSTEM AND METHOD FOR OPTICALLY ANALYZING LIGHT FROM A SAMPLE

BACKGROUND OF THE INVENTION

1. Field of the Invention

This invention relates to an optical system for analyzing light from a sample holder. The optical system is particularly suitable for use in a single or multi-channel separation system. The present invention is also directed toward a method of optically analyzing light from a separation system using a spectrograph.

2. Background

Spectrographs are devices for separating electromagnetic radiation into its spectral components. Optical spectrographs can be used for analysis of samples, such as analyzing the chemical composition of nucleic acid samples in order to determine the nucleotide sequence of the sample. Currently, experiments in chemistry and biology typically involve evaluating large numbers of samples. Sequencing of nucleic acid samples is typically time consuming and labor intensive. Therefore, it is desirable that a large number of samples can be simultaneously analyzed. With large scale projects such as the Human Genome Project, it is desirable to increase throughput of nucleic acid sequencing.

Electrophoresis is an increasingly common method of performing analysis, e.g. sequencing, of biological substances in order to increase throughput. Electrophoresis is an electrochemical process in which molecules with a net charge migrate in a solution under the influence of an electric current. Electrophoresis using one or more capillaries which are illuminated by a laser has proven to be useful in analyzing biological substances. Existing systems are typically not well-adapted for imaging large numbers of samples with a small focal ratio and high light collecting ability. Therefore, there is a need for an apparatus and method that maintains a substantially uniform image quality over a large field of view. Preferably, such an apparatus is compact, simple, and reduces focusing problems.

SUMMARY OF THE INVENTION

The advantages and purposes of the invention will be set forth in part in the description which follows, and in part will be obvious from the description, or may be learned by practice of the invention. The advantages and purposes of the invention will be realized and attained by the elements and combinations particularly pointed out in the appended claims.

To attain the advantages and in accordance with the purposes of the invention, as embodied and broadly described herein, the invention includes an optical system for analyzing light from a plurality of samples. The optical system includes a plurality of sample holders, a collection lens, a reimaging lens, and a light dispersing element located between the collection lens and the reimaging lens. The collection lens is configured to receive and substantially collimate light from the samples. The light dispersing element is configured to spectrally disperse the substantially collimated light from the collection lens. The reimaging lens is configured to receive light from the light dispersing element and direct the light onto a light detection device.

In another aspect of the present invention, the invention is directed towards a system for analyzing light from a sample in a separation system. The system includes at least one separation lane, a collection lens, a reimaging lens, and a light dispersing element located between the collection lens and the reimaging lens. The light source provides an excitation light to the at least one separation lane. The collection lens is configured to receive and substantially collimate light emitted from the separation lane. The light dispersing element is configured to spectrally disperse substantially collimated light from the collection lens. The reimaging lens is configured to receive dispersed light from the light dispersing element and direct the light onto a light detection device. In certain embodiments, the system may include a light source providing an excitation light to the at least one separation lane. In certain embodiments, the system may include a plurality of the separation lanes.

In yet another aspect of the present invention, the invention includes an optical spectrograph for analyzing light from at least one sample. The optical spectrograph includes at least one source of excitation light for illuminating at least one sample holder, a first lens unit, a transmission grating, a second lens unit, and a light detection device having a plurality of detector elements. The first lens unit has at least one lens and is configured to receive and substantially collimate light from the sample holder. The excitation light from the source of illumination does not pass through the first lens unit prior to illuminating the at least one sample holder. The transmission grating is configured to spectrally disperse substantially collimated light from the first lens unit. The second lens unit has at least one lens and is configured to receive light from the transmission grating and direct the light onto the light detection device.

In a further aspect of the present invention, the invention is directed toward a method of optically analyzing at least one sample. The method includes providing at least one holder having a sample therein, illuminating the sample with an excitation light to generate an emission light, and collecting the emission light from the sample with a collection lens. In certain embodiments of the method, the excitation light does not pass through the collection lens prior to illuminating the sample. The emission light is substantially collimated by the collection lens. The method further includes spectrally dispersing the substantially collimated emission light beam with a transmission grating, directing the emission light from the transmission grating onto a light detection device by a reimaging lens, and optically detecting the spectral characteristics of the emission light. In certain embodiments, a plurality of sample holders are provided.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain principles of the invention. In the drawings.

FIGS. 5A and 5B are schematics illustrating the effect of a light source being positioned at the optical axis and offset perpendicular from the optical axis, respectively, as the light passes through a collection lens;

FIGS. 6A and 6B are schematics illustrating the light rays of FIGS. 5A and 5B, respectively, passing through a reimaging lens onto a light detection device;

FIGS. 7A and 7B are schematics illustrating the effect of a light having different wavelength components, such as blue and red light, respectively, as the light passes through the collection lens;

FIGS. 8A and 8B are schematics illustrating the blue and red components of FIGS. 7A and 7B, respectively, passing through the reimaging lens onto a light detection device;

FIG. 9 illustrates incident light being spectrally dispersed by a transmission grating;

DESCRIPTION OF PREFERRED EMBODIMENTS

Reference will now be made in detail to several preferred embodiments of the invention, examples of which are illustrated in the accompanying drawings. Wherever possible, the same reference numbers will be used throughout the drawings to refer to the same or like parts.

According to certain embodiments, the present invention provides an optical system for analyzing light from a plurality of samples. According to certain embodiments of the invention, the optical system generally includes a plurality of sample holders, a collection lens configured to receive and substantially collimate light from the sample holders, a light dispersing element such as a transmission grating configured to spectrally disperse the substantially collimated light from the collection lens, and a reimaging lens configured to receive the light from the light dispersing element and direct the light onto a light detection device. Preferably, the sample holders are located substantially at the image plane of the collection lens. In certain embodiments, the optical system is used in a separation system having a plurality of separation lanes.

The present invention further provides methods of optically analyzing at least one sample in a spectrograph. The method includes providing at least one sample holder having a sample therein, illuminating the sample with an excitation light to generate an emission light, and collecting the emission light from the sample with a collection lens. In certain preferred methods, the excitation light does not pass through the collection lens prior to illuminating the sample. The emission light is substantially collimated by the collection lens. The method further includes spectrally dispersing the substantially collimated emission light with a light dispersing element, such as a transmission grating, directing the emission light from the light dispersing element onto a light detection device by a reimaging lens, and optically detecting the spectral characteristics of the emission light.

Figure 1:
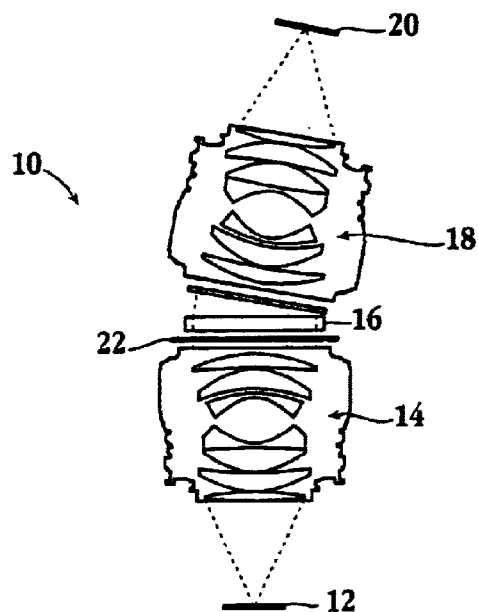
FIG. 1 is a side view of an optical system for analyzing light according to certain embodiments of the present invention.

FIG. 1 shows an example of an optical system for analyzing light from a sample according to certain embodiments of the present invention. As embodied herein and shown in FIG. 1, optical system 10 includes at least one sample holder, with a sample contained therein. The sample is preferably located at or near the object plane 12. The object plane is a plane at the focal distance from the collection lens 14. The optical system further includes a collection lens 14, a light dispersing element 16, a reimaging lens 18, and an optical detection device 20. In the example shown in FIG. 1, the optical system further includes an excitation light blocking filter 22 positioned between the collection lens 14 and the light dispersing element 16.

Figure 2:
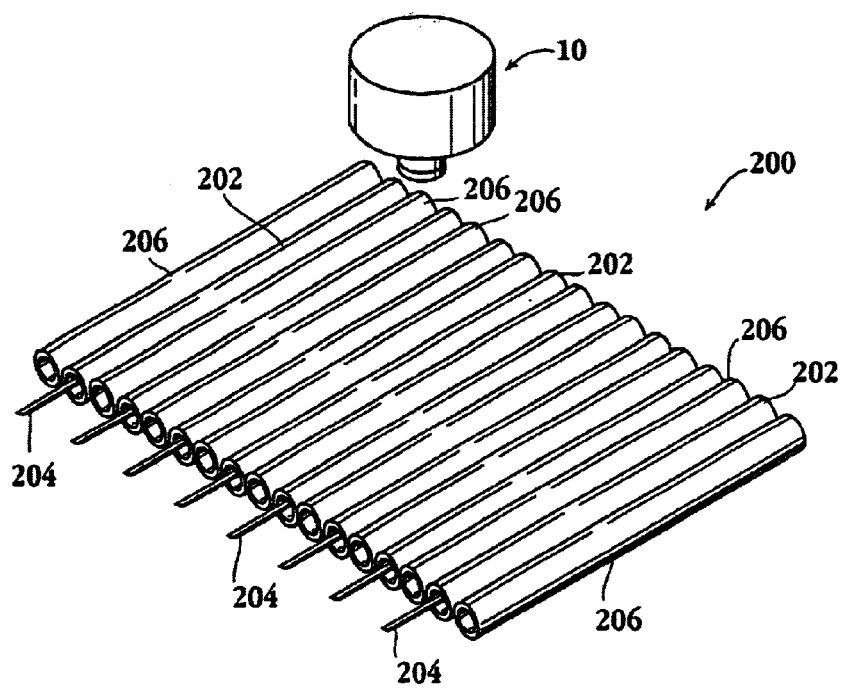
FIG. 2 is a perspective view of an array of capillaries of a separation system which may be used with the present invention.

In accordance with the present invention, the optical system includes at least one sample holder for containing a sample. The present invention will be described herein for use with a plurality of sample holders. However, the present invention is also suitable for use with a single sample holder. In certain preferred embodiments, the sample holders comprise a plurality of separation lanes, such as electrophoresis capillaries, located within the object plane of the collection lens. A separation lane is a path along which migrating sample components are separated, for example, using electrophoresis, chromatography, sedimentation, or other separation processes. FIG. 2 shows an example of a capillary arrangement suitable for use with the optical system of certain embodiments of the present invention. This capillary arrangement is known in the art, and is used for purposes of example only. The capillary arrangement shown in FIG. 2 is described in greater detail in U.S. Pat. No. 5,498,324 to Yeung et al., the disclosure of which is hereby incorporated in its entirety herein for any purpose. Other similar capillary arrangements are described in U.S. Pat. No. 5,938,908 to Anazawa et al., the disclosure of which is also hereby incorporated in its entirety herein for any purpose.

As embodied herein and shown in FIG. 2, the capillary system 200 is particularly suited for capillary electrophoresis. The capillary system 200 includes an array of capillaries 202 with optical fibers 204 inserted into an outflow end of the capillaries 202. In certain embodiments, a laser is directed at the ends of the optical fibers. Spacing capillaries 206 with black coating are placed between each of the capillaries 202 used for separation. Spacing capillaries 206 act as spacers to prevent crosstalk between separation capillaries 202. This capillary system is described in greater detail in U.S. Pat. No. 5,498,324 to Yeung et al. In certain capillary arrangement embodiments, sixteen capillaries are provided. This number may be varied to range from one to several hundred, depending on the field of view and size and quality of the optical system.

Other types of sample holders could be used including oligonucleotide arrays as described for example in U.S. Pat. No. 5,445,934 to Fodor et al., and microfluidic devices as described for example in WO97/36681 to Woudenberg et al., the disclosures of which are both hereby incorporated by reference in their entirety herein for any purpose. Other types of sample holders suitable for use with the present invention, include, but are not limited to, wells, slides, test tubes or any other sample holding device able to confine a sample to a known location. As generically shown in FIG. 2, an optical system 10 of the present invention may be positioned perpendicular to the capillary array.

Certain embodiments of the present invention also include an excitation source such as a laser for generating an excitation light to illuminate the sample (or samples) in the sample holder (or sample holders). One or several excitation sources may be provided. In certain particular embodiments using capillary tubes for holding the samples, excitation is provided to the sample by an Argon ion laser as discussed generally above, and in greater detail in U.S. Pat. No. 5,498,324 to Yeung et al. Other types of conventional excitation sources may also be used, such as an arc lamp (e.g., mercury/xenon lamp, mercury vapor lamp), xenon lamp, tungsten/halogen lamp, deuterium lamp, light emitting diode (LED), or high-intensity discharge (HID) lamp. The excitation source is typically selected to emit excitation light at one or several wavelengths or wavelength ranges absorbed by the sample or samples. In one specific example, lasers having a wavelength of 488 and 514 nm are used.

When the sample is illuminated by a laser or other excitation source, the sample acts as a light source and emits an emission light. In certain particular embodiments, two lasers are used. The provision of a laser or excitation source on opposite sides of the capillaries in certain embodiments helps to provide a more uniform intensity across a row of samples. Some applications of the present invention do not require an excitation source in order to illuminate the sample. For example, in chemiluminescence and electrochemiluminescence, a sample emits light without an excitation light source.

Preferably, the sample (or samples) is located at approximately the focal distance (at the object plane) from the collection lens 14 so that the light emitted from the sample (the emission light) upon being struck with an excitation light (e.g., laser beam) will be optimally collected by the collection lens 14. The sample is preferably positioned at or near the object plane of the collection lens.

The collection lens 14 is configured to receive and substantially collimate light from at least one sample holder. The collection lens is a type of lens that is spaced from the sample and that can collect light. An emission light from the sample is collected by the collection lens and directed toward a light dispersing element. The collection lens 14 may include a single lens or an assembly of multiple lenses, but will be referred to as a single lens for purposes of illustration. Because the collection lens is a collimating lens, light from the sample holder(s) will be converted into substantially parallel (or collimated) light rays as it passes through the collection lens. With a collimating lens such as collection lens 14, if a source of light (e.g., capillary tube) is centered on the optical axis 15 of the collection lens at the object plane 12, the emission light from the sample will be collimated along the optical axis 15 of the collection lens 14, as shown in FIG. 5A.

If the same point source of light is now moved to the side of the optical axis 15 along the object plane 12, as shown in FIG. 5B, the emission light will be collimated but at an angle θ to the optical axis 15 of the collection lens 14. Each point on the collection lens' object plane 12 (within the field of view of the lens) maps to a unique angle θ as light emitted from the point passes through the collection lens. Therefore, in the system of the present invention, a plurality of spaced-apart sample holders (e.g., capillary tubes) may be imaged by the same collection lens. A collimating lens such as the collection lens 14 functions to convert spatial information into angular information.

Figure 3:
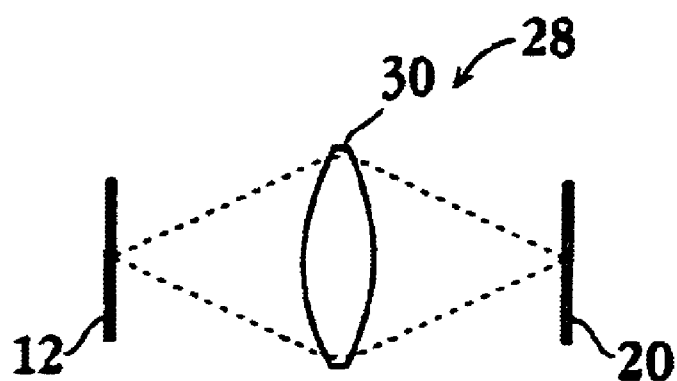
FIG. 3 is a schematic of an optical system having a single lens.
Figure 4:
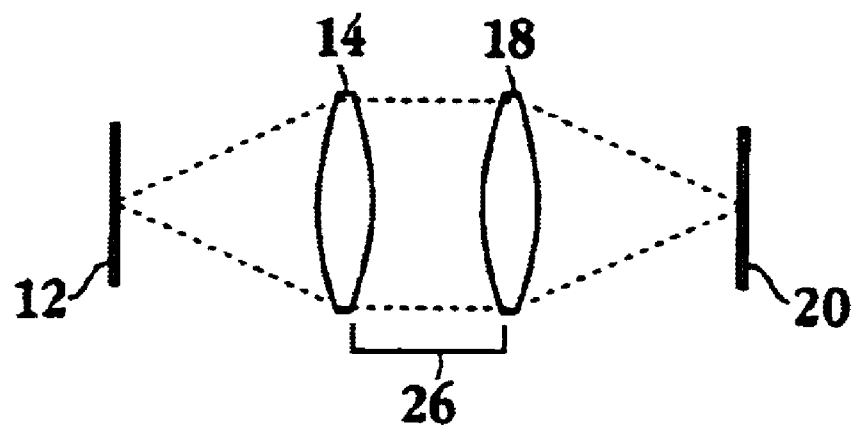
FIG. 4 is a schematic of an optical system according to the present invention having two lenses.

The use of a collimating lens such as collection lens 14 provides a substantially collimated region 26 as shown in FIG. 4. The light is substantially collimated in the region between the collection lens 14 and reimaging lens 18. The collimated region is particularly well suited for the insertion of a variety of optical devices (e.g., apertures, interference filters, etc.). An optical lens system with a plurality of lenses (e.g., a relay lens system) can provide advantages over a single lens system 28 such as shown in FIG. 3. In a single lens system, one lens 30 both collects light from an object plane 12 and refocuses the light to an image plane 20. The single lens system cannot provide a collimated region for the insertion of optical devices, a disadvantage compared to the present invention.

A lens that may be used as a collection lens in the present invention include, but are not limited to, any positive lens, i.e., a lens that brings collimated light to a focus. These positive lenses may include, for example, a still camera lens, a CCD video camera lens, a microscope objective, or an achromatic lens.

In accordance with the present invention, a light dispersing element may be provided, along with other optical devices, in the substantially collimated region 26 between the collection lens 14 and reimaging lens 18. As discussed above, the collection lens substantially collimates the light and directs it to the light dispersing element. A light dispersing element can be any element that spectrally separates incoming light into its spectral components. For example, incoming light can be deflected at an angle roughly proportional to the wavelength of the light. Thus, different wavelengths are separated.

For the sake of illustration only, the light dispersing element discussed will be a transmission grating. In a transmission grating, the light rays that strike the grating surface are transmitted through the grating. In general, rays of light that strike a transmission grating surface deflect at an angle roughly proportional to the wavelength of the light. The transmission grating can be of several types, such as a flat blazed grating. Blazed gratings have a triangular, sawtooth shape. The shape of each groove functions like a prism to refract the light. Typically, a grating will have hundreds or thousands of grooves per mm. In certain particular embodiments, the grating groove density may range from about 100 grooves/mm to about 1,200 grooves/mm. This range is for purposes of example only, as larger and smaller groove densities may also be used with the present invention.

In a transmission grating, the rays of light pass through the grating and are spread spectrally as is known in the art. FIG. 9 illustrates an incident light 40 striking a transmission grating and being dispersed spectrally into a plurality of distinct light rays 42, 44, 46, 48, each corresponding to a particular wavelength component of incident light 40.

This concept is further illustrated in FIGS. 7A and 7B. FIGS. 7A and 7B show light being emitted from a point on the object plane at the optical axis 15 of the collection lens 14. The emission light is collimated by the collection lens 14 and strikes the transmission grating 16. When the collimated light strikes the transmission grating, the light is dispersed spectrally. With spectral dispersion, a first light ray of a first wavelength will be deflected at a different angle with respect to the optical axis than a second light ray of a second wavelength. This effect is illustrated in FIGS. 7A and 7B, where the components of the light having a wavelength corresponding to blue are deflected at a different angle than the components of the light having a wavelength corresponding to red. The blue rays will remain collimated, as will the red rays, but at different angles with respect to the optical axis of the collection lens and with respect to each other.

The light dispersing element spreads the light spectrally in a direction substantially perpendicular to the spectral channels on the light detection device. This configuration creates a two-dimensional image on the light detection device after the light passes through the reimaging lens 18; in the first direction the light is spectrally dispersed, in a second direction the light is spatially resolved/separated. The light forms a plurality of images corresponding to channels on the light detection device so that the light from each channel may be analyzed for its spectral components.

A variety of other types of light dispersing elements, such as reflection gratings or prisms may be used with the present invention, although a transmission grating is preferred. The basic principles of the present invention are applicable with a variety of other types of light dispersing elements such as prisms, grating prisms ("grisms"), and one or more dichroic filters.

The light dispersing element disperses the collimated light and directs the light toward a reimaging lens. The reimaging lens 18 receives the spectrally dispersed, but still collimated, light from the light dispersing element and directs it to the light detection device. The reimaging lens 18, also known as a focusing lens in certain embodiments, takes a collimated light and directs it at or near a point on the image plane of the reimaging lens. In certain embodiments, the reimaging lens 18 is optically identical to the collection lens 14, except that the lens are reversed in direction so that they face each other. The image formed by the reimaging lens on the light detection device may be at a 1:1 ratio with the sample being analyzed, or it may be magnified or demagnified.

As illustrated in FIGS. 6A and 6B, the reimaging lens 18 receives the substantially collimated light from the collection lens, and directs the light toward an image plane 20. In a manner similar to the collection lens, if the incident collimated light is centered along the optical axis 19 of the reimaging lens 18, the light will be focused on the image plane 20 at the optical axis 19 of the reimaging lens, as shown in FIG. 6A. However, if the incident collimated light is angled relative to the optical axis 19 of the reimaging lens 18 (such as shown in FIG. 5B), the light will be focused on or near the image plane offset from the optical axis 19 of the reimaging lens, as shown in FIG. 6B. The angle of the collimated light relative to the optical axis 19 of the reimaging lens determines a unique location on the image plane 20 of the reimaging lens (within the field of view). The angular displacement of the light from the collection lens is converted into a spatial displacement on the light detection device (e.g., CCD) by the reimaging lens. In this manner, the optical system can focus light from a plurality of light sources (e.g., a plurality of illuminated capillary tubes).

As described in relation to FIGS. 7A and 7B, light from a given sample typically includes components having different wavelengths. As shown for example in FIGS. 8A and 8B, these different components (blue and red in the example shown) will remain collimated after passing through the light dispersing element. As shown in FIG. 8A, when the blue collimated rays pass through the reimaging lens, the blue rays will be focused onto a first location on the image plane 20. As shown in FIG. 8B, the red collimated rays also pass through the reimaging lens and are focused on a second location on the image plane 20. The second location is displaced from the first location. This effect occurs for each of the different wavelengths of light rays, so that a spectrum is created for each individual sample (e.g., capillary tube). The spectrum for each capillary tube (or other type of sample holder) that is formed on the light detecting device is referred to as a channel. The number of channels corresponds to the number of capillary tubes in the field of view.

Preferably, in certain embodiments, the image plane of the reimaging lens is located coplanar with the light detection device 20 for optimized detection. A light detection device analyzes light from a sample for its spectral components. In certain embodiments, the light detection device comprises a multi-element photodetector. As used herein, the term means a detector having a plurality of addressable detector elements. Exemplary multi-element photodetectors may include, for example, charge-coupled devices (CCDs), diode arrays, photo-multiplier tube arrays and charge-injection devices (CIDs). A CCD is typical if a plurality of samples are being simultaneously analyzed because it can provide an area for a plurality of channels (e.g., one channel for each sample). The light dispersing element, specifically a transmission grating in certain embodiments, spectrally spreads the light from each capillary tube so that it can be spectrally analyzed by a CCD. However, if only one sample or capillary tube is used, it may be desirable to use a single photosensor.

As previously discussed, if a plurality of samples are simultaneously analyzed, a corresponding number of channels will be formed on the light detecting device. In certain embodiments, these channels will be formed as parallel channels. An optical detection device such as a CCD has an array of detection units, or pixels, arranged on a planar surface. A CCD will typically have a large number of pixels, usually several hundred in each of the two axis. Each pixel will map to a specific channel or portion thereof and specific color (wavelength) of light from a sample in a specific capillary.

Figure 10:
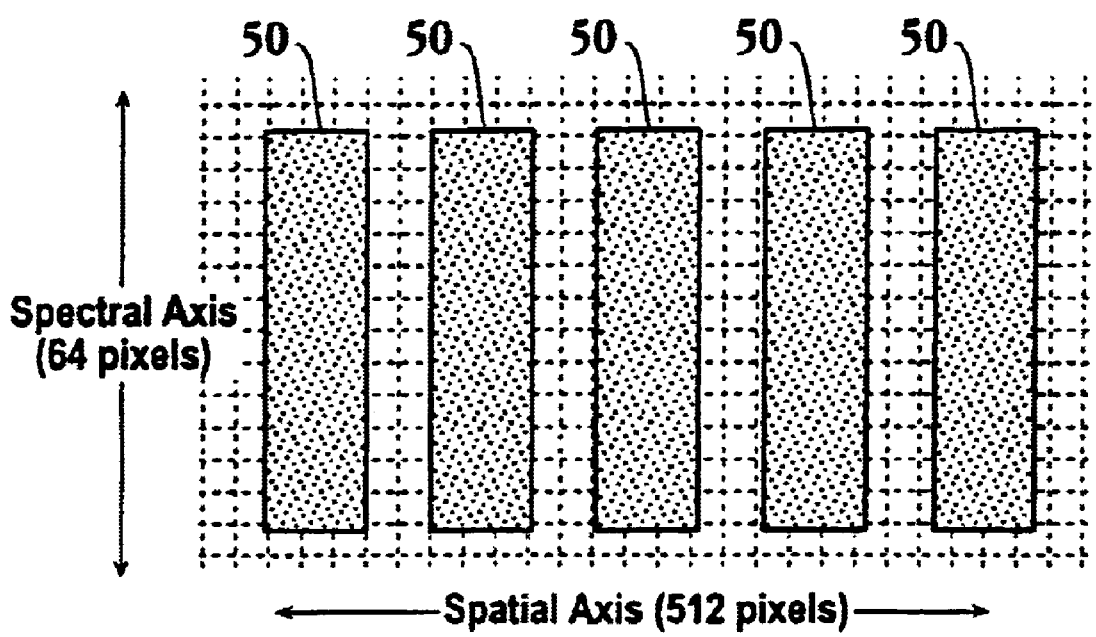
FIG. 10 illustrates the channels on an optical detection device such as a CCD, according to certain embodiments of the present invention.

In certain embodiments, the CCD has two axes: a spatial axis and a spectral axis. This is shown in FIG. 10 which illustrates an example with five channels 50 on the CCD. Each channel spaced along the spatial axis (x-axis) corresponds to an individual capillary tube. For example, if sixteen capillary tubes are used, there will be sixteen channels on the CCD. In certain embodiments, it is preferred to analyze the center of the sample to get the most accurate results, therefore only the pixels at or adjacent the center of each channel will be analyzed. In certain embodiments of the present invention, the capillary tubes have an inner diameter of approximately 50 μm, which corresponds to about two or three pixels. The spectral axis (y-axis) contains spectral information (e.g., wavelength vs. intensity information) for each of the capillary tubes. The axes could also be reversed if desired.

The optical system may further include one or more blocking filters to prevent significant amounts of excitation light or other background light (e.g., Raman light, ambient light, etc.) from reaching the light detecting device. In certain embodiments, in order to block scattered excitation light from causing noise (e.g., optical shot noise) in the system, one or more excitation blocking filters, such as long-pass filters, may be provided in the emission optical path. Excitation blocking filters prevent certain types of excitation light from entering the emission optical path of the optical system. FIG. 1 shows an excitation blocking filter 22 positioned between the collection lens 14 and the transmission grating.

Several types of filters such as interference filters and colored glass filters may be used as excitation blocking filters in the optical system. There are several types of interference filters such as notch, long-pass, and band-pass filters. There are also several types of colored glass filters such as long-pass and band-pass filters Interference filters may be configured to significantly block wavelengths below a predetermined threshold from passing to the reimaging lens. Excitation blocking filters may also be placed at a variety of other positions, such as prior to the collection lens (e.g., between the sample and the collection lens). The collimated region is particularly suited for interference filters, because interference filters typically operate most efficiently when the incident light striking the filter is perpendicular to the surface of the filter (and the light is collimated). An interference filter in the collimated region will preferably be positioned between the collection lens and the transmission grating. One may use more than one excitation blocking filter at different positions, or may use one excitation blocking filter at any of the possible positions.

Figure 11A:
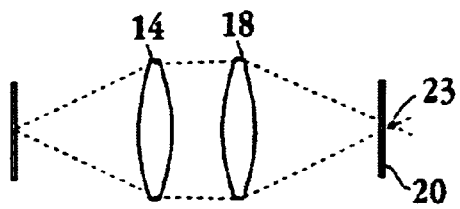
FIGS. 11A–11C illustrate the position of an image relative to the desired image plane for light having a long wavelength, medium wavelength, and short wavelength, respectively.
Figure 11B:
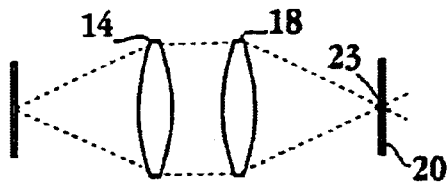
Figure 11C:
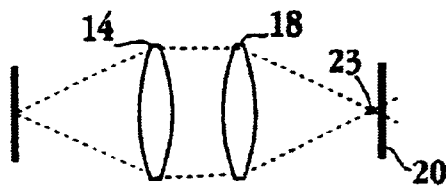

The present invention may also be particularly configured to reduce chromatic aberration. Chromatic aberration is a variation in focal length (and focus quality) with wavelength. Chromatic aberration may be particularly troublesome with wavelengths in the non-visible range, such as infra-red or near infra-red wavelengths. FIGS. 11A–11C illustrate the effect of wavelength on the extent of chromatic aberration as represented by the position of the focal point 23 relative to the mid-wavelength image plane 20 of reimaging lens 18. FIG. 11A demonstrates that for a longer wavelength, the position of focal point 23 is beyond the mid-wavelength image plane 20. FIG. 11B demonstrates that for a middle, optimum wavelength, the position of focal point 23 occurs at the mid-wavelength image plane 20. FIG. 11C demonstrates that for a short wavelength, the position of focal point occurs before the mid-wavelength image plane 20.

Figure 12:
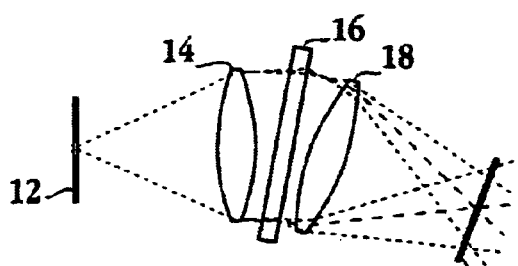
FIG. 12 is a schematic illustrating the effect of chromatic aberration on focusing in certain embodiments of the present invention.

FIG. 12 illustrates a possible effect of chromatic aberration on the performance of the optical system. As shown in FIG. 12, the light rays in the center of the image plane (at the optical axis of the reimaging lens) will be focused, while those at the edges will be out of focus. It is desirable to minimize chromatic aberration (i.e., have the light rays focused on the light detection device at both the center and the edges of the image plane) in order to increase the quality of the image obtained.

Figure 13:
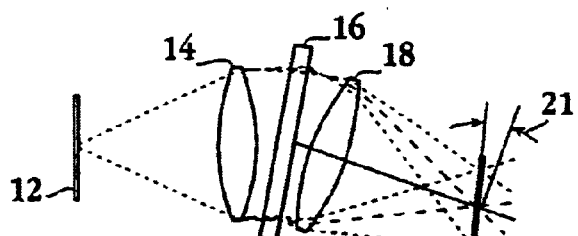
FIG. 13 is a schematic illustrating the effect of tilting a detection plane of a CCD to reduce chromatic aberration.

According to certain embodiments of the present invention, tilting the plane of the light detection device 21 (or other elements along the optical path) can assist in reducing chromatic aberration as described in FIG. 12. As shown in FIG. 13, tilting the planar surface 21 of the light detecting device (CCD) by a slight angle with respect to the optical axis of the collection lens compensates for chromatic aberration, thereby improving the quality of the image on the CCD over a wider spectrum of the light wavelength. Other adjustments besides tilting the planar surface of the light detection device may also be used in order to minimize the effect of chromatic aberration on the quality of the image. For example, one or both of the collection lens and transmission grating may be tilted with respect to the optical axis of the collection lens. Moreover, any of the filters may be also be tilted with respect to the optical axis of the collection lens. In certain embodiments, it is desirable to be able to adjust all of the optical elements in order to bring an image into sharper focus.

The tilting of the light detection device also assists in reducing the amount of stray light that is reflected off of the light detection device back into the system. Stray light may reduce the desired signal to noise values or cause channel to channel cross-contamination. Another method of reducing stray light, besides tilting the light detection device, is to provide anti-reflective coating on the light detection device. The anti-reflective coating may be provided on the window of the light detection device, or on the planar surface of the light detection device itself. It may also be desirable to provide an anti-reflective coating on any and all of the elements that the light passes through.

Figure 14:
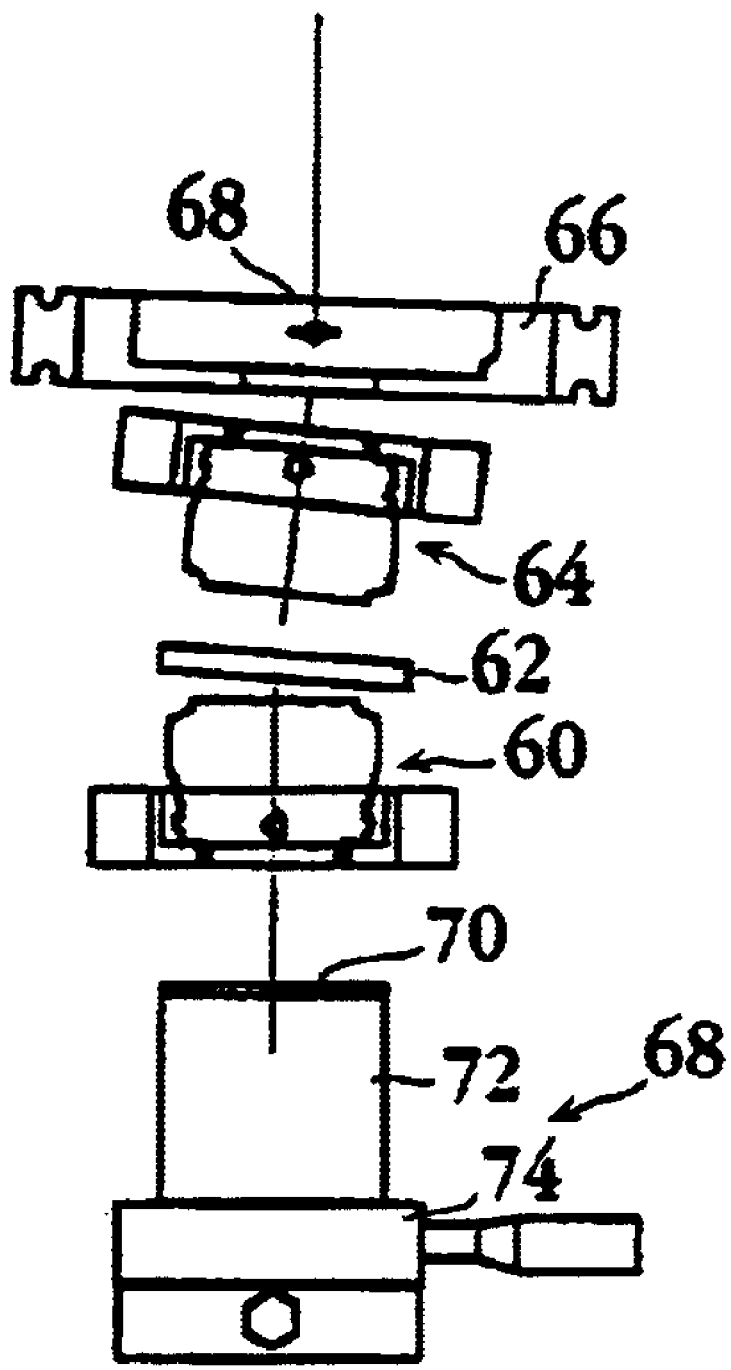
FIG. 14 is a side view of a system for testing the amount of tilting of the detection plane of the CCD to bring the image into focus.

In accordance with certain embodiments of the present invention, a device and technique for determining the optimal angle of tilt of a planar light detection device is provided. In this technique, the detection device, e.g., CCD, may be tilted at various angles and the resulting images examined for focus quality along a spectral axis of the light detection device. The focus along the edges of the image is then compared to the focus in the center of the image. As embodied in certain embodiments shown in FIG. 14, the system includes a collection lens 60, transmission grating 62, reimaging lens 64, and charge-coupled device (CCD) 66, which may be identical to the collection lens 14, transmission grating 16, reimaging lens 18, and charge-coupled device at image plane 20, respectively, of the system previously described for FIGS. 1–13. In the testing apparatus, the charge-coupled device 66 is tilted by pivoting about rotational axis 68 shown in FIG. 14. The device for measuring the effect of the tilting includes a test aperture 70 with a light diffuser, a light source 72 such as a neon bulb, and an x-y stage 74. It was discovered that a slight change in the angle of the CCD may substantially reduce the amount of chromatic aberration in the optical system.

Figure 15:
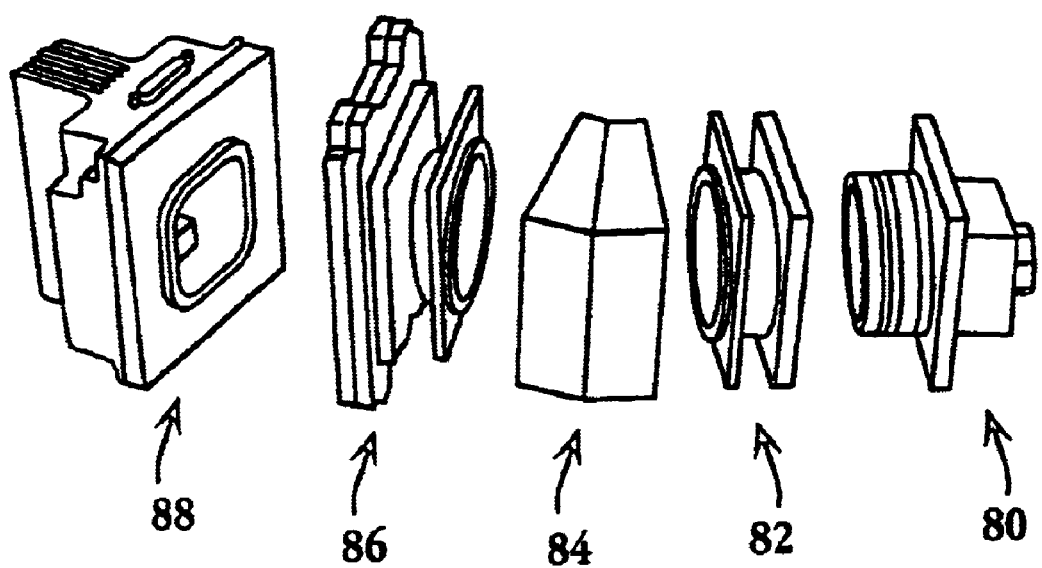
FIG. 15 is a perspective view of an optical system according to an embodiment of the present invention.

One particular example of the optical system of the present invention is illustrated in FIG. 15. The system shown in FIG. 15 is by way of example only, and is not meant to be limiting in any manner. As embodied herein and shown in the example of FIG. 15, the optical system includes a collimating assembly 80 with a collimating lens therein, a grating assembly 82 with a transmission grating therein, an angle assembly 84, a focusing assembly 86 with a reimaging lens therein, and a CCD assembly 88. In this particular example, the collating assembly 80 and focusing assembly 86 include camera lenses, such as Nikon camera lenses with an aperture speed of f/1.4. Camera lens having higher or lower aperture speeds, such as f/1.2, for example, are also suitable with the present invention. In the example shown in FIG. 15, the camera lens each have a focal length of 50 mm.

The grating assembly 82 includes a transmission grating similar to transmission grating 16 previously described. In the example of FIG. 15, the transmission grating has a ruling of 600 grooves/mm. The angle assembly 84 may include optical elements such as one or more correction lenses, apertures, or gratings. Preferably, the angle assembly 84 is configured to be angled to match the amount of diffraction caused by the transmission grating in the grating assembly 82 at a mid-wavelength of interest. The CCD assembly 88 includes a charge coupled device as previously described. The CCD has a pixel spacing of 24 $\mu$m/pixel and an array of 512×250 pixels. Moreover, the optical system includes an interference filter (not shown in FIG. 15) positioned between the collimating assembly 80 and the object plane of the sample. The optical system also includes a second interference filter (not shown in FIG. 15) positioned between the collimating assembly 80 and the grating assembly 82. These two interference filters may be identical. The optical system of FIG. 15 is for purposes of example only.

In the present invention, the optical components may be mounted in any matter known in the art. For example, the components may be placed on supports or other mechanical supporting means and attached to an optical table.

In accordance with other embodiments of the present invention, the optical system may include a correction lens. A correction lens can reduce the curvature of the field of focus at the image plane of a lens optimized for a larger field of view than required for the present invention. As embodied herein and shown in FIG. 17, a correction lens 90 may be positioned between the collection lens 14 and the reimaging lens 18. The correction lens may be utilized in particular systems in which curvature is an issue. In the optical system of FIG. 16, the combination of camera lenses 14 and 18 typically result in an overcorrected focus field curvature, such as shown in dashed lines by reference numeral 92. This curved field of focus does not typically cause problems in photographic applications. However, in an optical system used for spectrography, the area of interest is limited to a small percentage of the area of interest typically used in normal photography.

Figure 16:
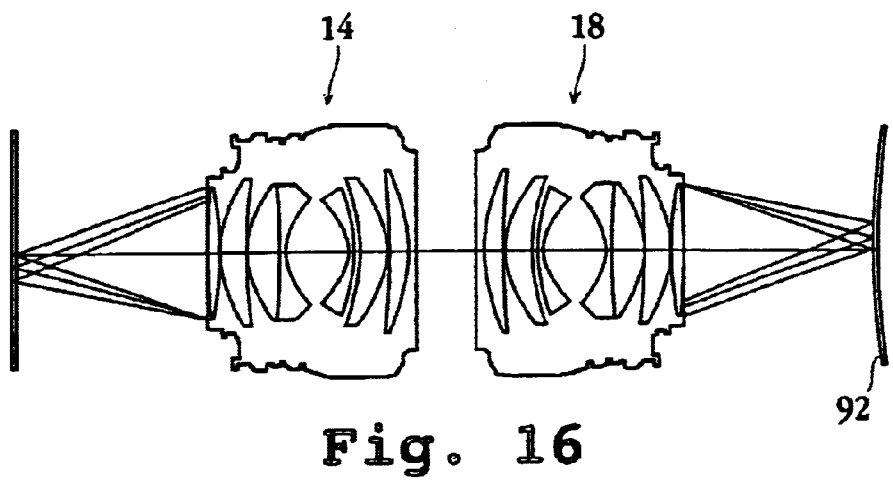
FIG. 16 is a side view of an optical system, illustrating the curved field of focus in certain systems that do not include a correction lens.
Figure 17:
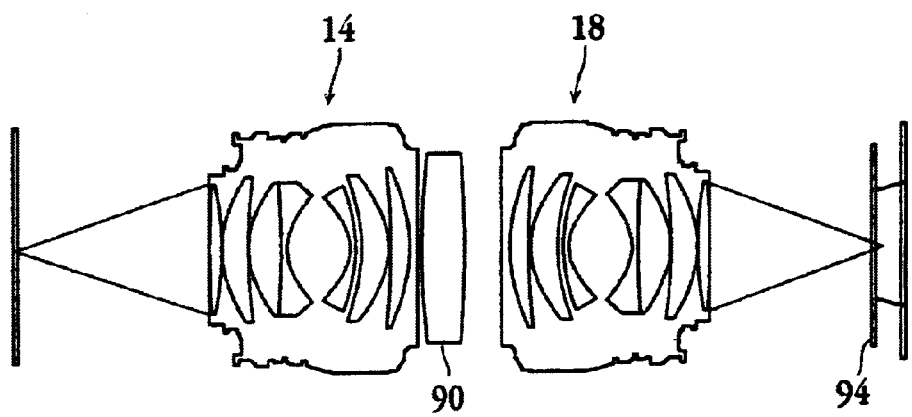
FIG. 17 is a side view of an optical system according to embodiments of the present invention, with a correction lens.

In order to compensate for the overcorrection of the system of FIG. 16, a correction lens 90 may be inserted between the collection lens 14 and the reimaging lens 18. In certain embodiments, the correction lens is a simple achromatic lens 90 as shown in FIG. 17. The correction lens typically should be configured to reduce the curvature of the field of focus, resulting in a substantially planar field of focus such as shown by reference numeral 94 in FIG. 17. Moreover, the correction lens typically should be configured to provide the collimated region as previously described. The use of a correction lens may result in a magnification or demagnification of the image, as shown in FIG. 17.

Figure 18:
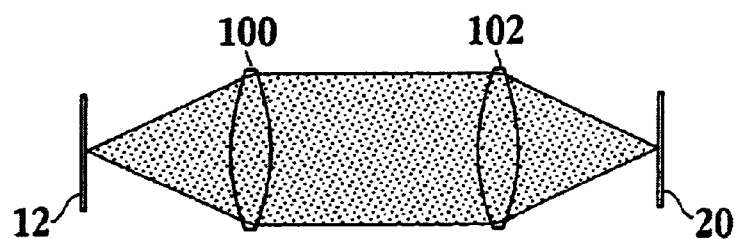
FIG. 18 is a schematic of an optical system with no vignetting.
Figure 19:
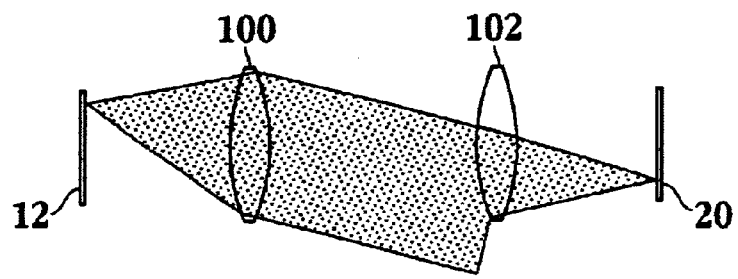
FIG. 19 is a schematic of an optical system with vignetting.

In accordance with other embodiments of the present invention, the optical system reduces variations in light throughput across the field of view, typically referred to as vignetting. Vignetting can be a limiting effect of an optical system where portions of entering light are not permitted to pass through the optical system because of structural obstacles. FIG. 18 illustrates an optical system with a full light throughput, with no vignetting. In FIG. 18, all of the light that enters the first lens 100 is fully transmitted to the second lens 102, without any structural obstacles blocking the light. FIG. 19 illustrates the effect of vignetting. In FIG. 19, the light source is located off-center from the optical axis of the first lens 100. Therefore, only a portion of the light is transmitted through the second lens 102 to the image plane 20. The light throughput of the optical system has dropped because of vignetting. With certain embodiments of the present invention, it may be desirable to reduce vignetting, particularly if capillaries (or other sample holders) are placed near the limits of the field of view of the collection lens.

Figure 20A:
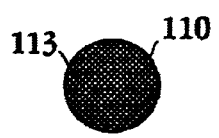
FIGS. 20A–20D are front views illustrating the effect of vignetting as the angle of the incident light becomes more offset.
Figure 20B:
Figure 20C:
Figure 20D:
Figure 21A:
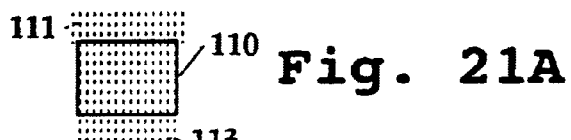
FIGS. 21A–21D are top views corresponding to FIGS. 20A–20D respectively.
Figure 21B:
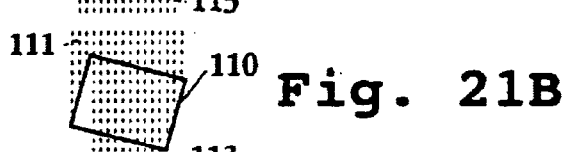
Figure 21C:
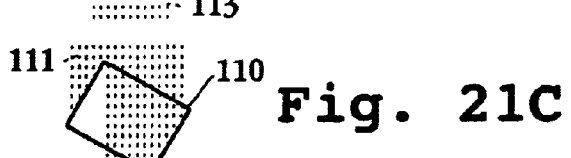
Figure 21D:
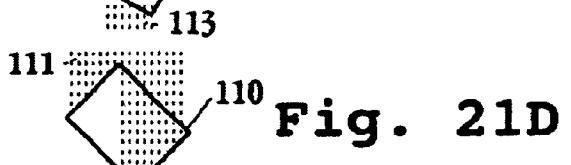

FIGS. 20A–20D and 21A–21D illustrate the effect of vignetting on a hypothetical system as the light source becomes more distant from the optical axis of the system. In this hypothetical system, the system is shown as 110. As shown in FIGS. 20A and 21A, all the incident light 111 will pass through the system 110 as exit light 113, when the light source is located exactly on the optical axis of the system. FIGS. 20B and 21B illustrate the light being at a slight angle to the optical axis of the system. As can be seen in FIGS. 20B and 20B, a small amount of the outer fringes of the incident light 111 will be clipped by the system. A large percentage of the incident light 111 exits as exit light 113 in the arrangement of FIGS. 20B and 21B, resulting in a small amount of vignetting. FIGS. 20C and 21C show an increase in the angle of the incident light relative to the system, and FIGS. 20D and 21D show an even greater increase in the angle of the incident light relative to the system. The amount of vignetting increases as the angle of the incident light 111 relative to the system optical axis increases. As is also clear from these drawings, the amount of light exiting the system (light throughput) decreases. In certain embodiments, it is desirable to avoid a decrease in light throughput in an optical spectrograph system.

Figure 22:
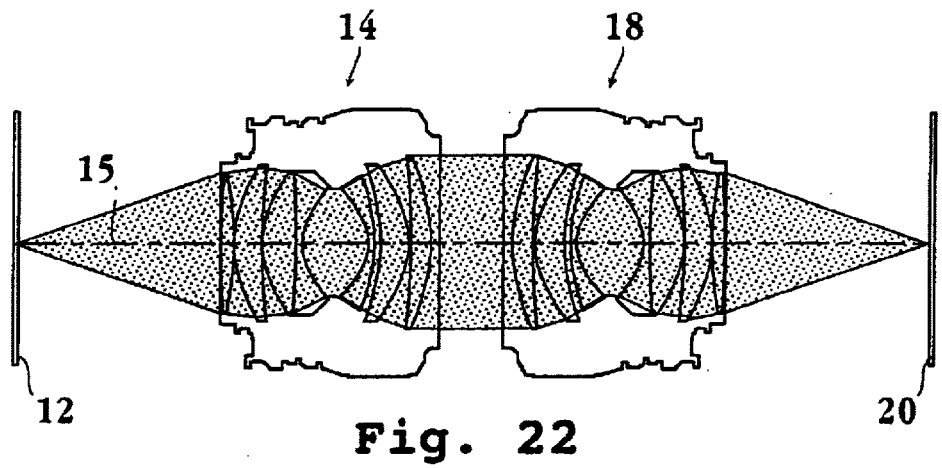
FIG. 22 is a side view of an optical system according to certain embodiments of the present invention with a light source on the optical axis so that no vignetting occurs.
Figure 23:
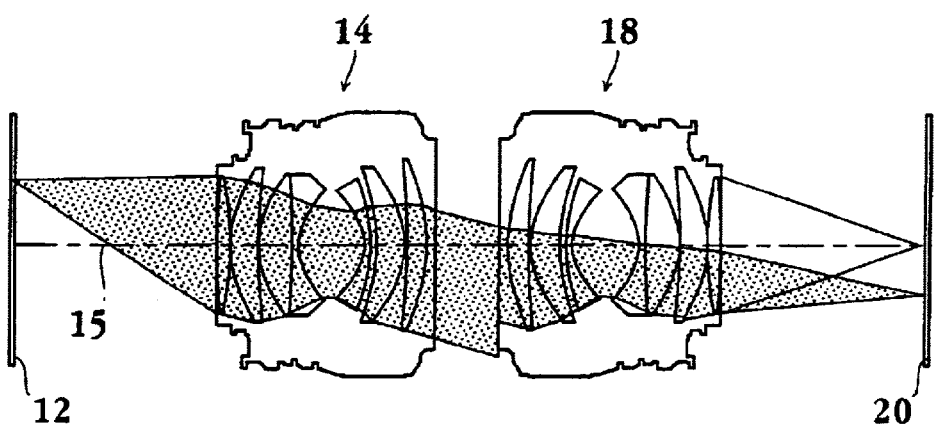
FIG. 23 is a side view of the optical system of FIG. 22 with the light source displaced from the optical axis so that vignetting occurs.

FIGS. 22 and 23 illustrate the possible effect of vignetting on an optical system with lenses similar to those previously discussed. FIG. 22 shows the light source being positioned on the optical axis of the collection lens 14. As seen in FIG. 22, emission light from the light source passes through the optical system to the image plane 20 without interference. In FIG. 23, the light source is positioned at the object plane, but spaced perpendicularly from the optical axis. As shown in FIG. 23, a portion of the light is blocked by the internal structure of the optical system. Therefore, a portion of the initial light is lost, and the light throughput decreases. The optical system of certain embodiments of the present invention is particularly configured to reduce vignetting by placing the reimaging lens 18 as close to the collection lens 14 as possible. This helps to reduce the amount of light that is blocked from passing through the system, thereby reducing vignetting.

Figure 24:
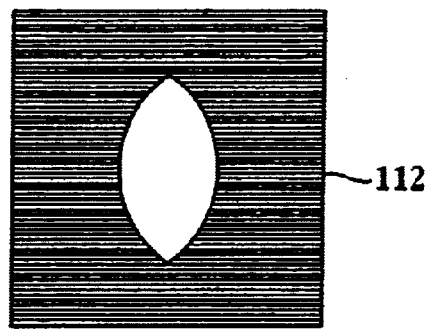
FIG. 24 illustrates a cat's eye aperture according to certain embodiments of the present invention.

Certain embodiments of the present invention are directed toward a device and method for reducing variations in light throughput in an optical system, which may be a result of excessive vignetting. As embodied herein and shown in FIG. 24, the optical system of certain embodiments of the present invention may include a light blocking aperture 112 positioned between the collection lens 14 and the reimaging lens 18. The light blocking aperture 112 is preferably positioned at approximately the position of filter 22 in FIG. 1, between the collection lens 14 and the light dispersing element 16. Preferably, the aperture 112 is configured to have a particular geometric shape such as the "cat's eye" or football shape shown in FIG. 24. The cat's eye is geometrically described as being two arcs joined at a top and bottom, with the width being the smallest at the top and bottom, and greatest at the middle. The "cat's eye" aperture is generally in the shape of an American football, as is shown in FIG. 24. In other embodiments, the aperture could be in other shapes such as circular.

In certain embodiments, the cat's eye aperture 112 is positioned exactly midway between the collection lens 14 and the reimaging lens 18. In certain particular embodiments, the cat's eye aperture 112 is positioned at the location where the excitation blocking filter 22 is shown in FIG. 1. The aperture blocks the light so that the amount of light that passes through is always substantially equal to the throughput of the worst off-axis rays striking the collection lens. This is illustrated in FIGS. 25 and 26. The cat's eye aperture allows substantially uniform light throughput even when the angle of the input rays vary substantially. The overall throughput of a system with this aperture will be lower compared to a system without an aperture, however this is acceptable in certain embodiments in view of the specifically stated advantages.

Figure 25A:
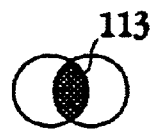
FIGS. 25A–25E are front views illustrating the effect of the cat's eye aperture of FIG. 24 on the light throughput of an optical system.
Figure 26A:
FIGS. 26A–26E are top views corresponding to FIGS. 25A–25E respectively.
Figure 25B:
Figure 26B:

FIGS. 25A–25E and 26A–26E demonstrate how, in a system with a cat's eye aperture, a substantially uniform light throughput occurs even though the angle of the incident light relative to the system varies. FIG. 25 illustrates the view looking down the optical system with the cat's eye aperture. FIG. 26 illustrates a top view of the system with a cat's eye aperture 112 positioned approximately midway through the system. FIGS. 25A and 26A illustrate the incident light 111 at its most off-axis (e.g., at its greatest angle to the optical axis of the system) position to the left of the system. A light throughput of a predetermined amount is permitted to pass through the optical system. The exiting light is represented as reference number 113. FIGS. 25B and 26B illustrate the light throughput when the incident light is at a lower angle relative to the optical axis of the system. As seen in the FIGS. 25B and 26B, the shape of the light that passes through the cat's eye aperture (and optical system) is identical to the shape of the light that passed through the cat's eye aperture in FIGS. 25A and 26A. The amount of light throughput therefore does not vary with the angle of the incident light.

Figure 25C:
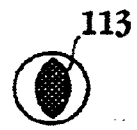
Figure 26C:
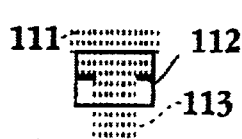
Figure 25D:
Figure 26D:
Figure 25E:
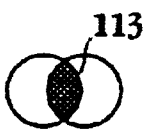
Figure 26E:

FIGS. 25C and 26C show the light throughput when the incident light is centered along the optical axis of the system. The shape of the light and the amount of throughput (shown as exit light 113) remains the same as for the previous positions. The same uniform light throughput is found at the positions shown in FIGS. 25D and 26D, and FIGS. 25E and 26E.

Uniform light throughput is an advantageous feature in an optical system for a spectrograph. With uniform light throughput for every light detection device channel (or every sample holder being analyzed), the dynamic range of the system may be increased. This is particularly true if the integration time of the system is adjusted to approach the full well charge capacity of the CCD during operation. Another advantage of the cat's eye aperture is that it reduces the f/number of the system a greater amount in the spatial dimension than in the spectral dimension. This increases the image quality in the spatial direction. Spatial image quality may be particularly important to optimize in order to reduce light from one channel from bleeding over into an adjacent channel.

In accordance with certain embodiments of the present invention, the optical system may include a first substantially hemispherical optical element positioned between the collection lens and the object plane of the collection lens. A hemispherical element similar to the hemispherical element of the present invention is described in ABI PRISM DNA Analyzer Service Manual, Revision A., the contents of which are hereby incorporated herein for any purpose. In certain embodiments, the optical system also includes a second substantially hemispherical optical element positioned between the reimaging lens and the image plane of the reimaging lens. The hemispherical element or elements assists in increasing the light collection efficiency of the optical system. The hemispherical element or elements preferably increases the aperture speed (f/number) of the system without degrading the image quality.

Figure 27:
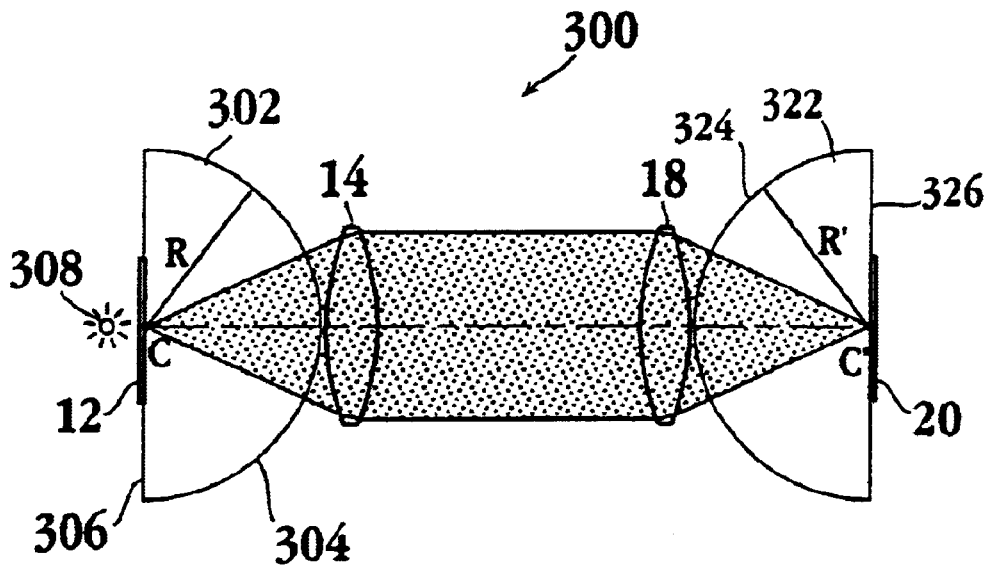
FIG. 27 is a schematic of an optical system according to an embodiment of the present invention, with a hemispherical element.

One embodiment of the optical system with at least one hemispherical element as shown in FIG. 27. As embodied herein and shown in FIG. 27, the optical system 300 includes a first hemispherical element 302 and a second hemispherical element 304. In certain embodiments, the first hemispherical element 302 includes a substantially hemispherical outer surface 304 and a flat surface 306 as shown schematically in FIG. 27. The hemispherical outer surface 304 has a radius of curvature R and a center of curvature at point C. Preferably, the center C of curvature of the hemispherical outer surface 304 is positioned at the light source (e.g., at the intersection of the optical axis 308 of the collection lens 14 and the object plane 12 of the collection lens 14). Alternately, the center of curvature C may be slightly spaced from the image plane 12 as shown in FIG. 27. In certain embodiments, it is desired to have the flat surface 306 be as close to the sample as possible. If a slide or other flat surface is used for the sample holder, the flat surface of the hemispherical element may be pressed against the surface of the sample holder. In other embodiments, the flat surface of the hemispherical element may be spaced from the top of the sample holder by a minimal amount. It is preferable for the radius of curvature of the hemispherical element to be as large as possible based on the spacing between the object plane 12 and the collection lens 14. As seen in FIG. 27, the radius of curvature R of the hemispherical element 302 is sized to be almost as large as the spacing between the collection lens 14 and the object plane 12.

The optical system 300 may further include a second hemispherical element 322. The second hemispherical element 322 includes a substantially hemispherical outer surface 324 and a flat surface 326 as shown schematically in FIG. 27. The hemispherical outer surface 324 has a radius of curvature R' and a center of curvature at point C'. Preferably, the center C' of curvature of the hemispherical outer surface 324 is positioned at the light detection surface (e.g., at the intersection of the optical axis 308 and the image plane of the reimaging lens 18.) Alternately, the center of curvature C may be slightly spaced from the image plane 12 as shown in FIG. 27. The second hemispherical element 322 functions similarly to the first hemispherical element 302.

The hemispherical elements are constructed of any optically transparent material such as glass and plastic. Preferably, these materials have a high index of refraction. Materials that are particularly suited for the hemispherical elements, include, for example, glasses such as flint glass and sapphire, and polymers such as polycarbonates. In certain embodiments, the index of refraction is uniform throughout the hemispherical element.

The hemispherical element 302 allows light rays to proceed from a point on the sample (positioned at the intersection of the optical axis 308 and the object plane 12), to exit the hemispherical element in a direction normal to the hemispherical outer surface 304 (i.e., the light rays travel from the center C of the radius of curvature to the hemispherical outer surface 304). As shown in FIG. 27, the angle of a given light ray exiting the hemispherical element to the collection lens 14 does not vary when it leaves the hemispherical element. By maintaining a straight path for the light rays (between the sample and the collection lens), aberration is minimized, so that focus is not affected. For samples that are spaced from the optical axis, the light rays passing through the hemispherical element and leaving the outer hemispherical surface 304 will be substantially normal, without significant aberration. The hemispherical element increases the percentage of the light from the sample that is available to reach the collection lens 14, thereby increasing the light throughput of the system.

Figure 28:
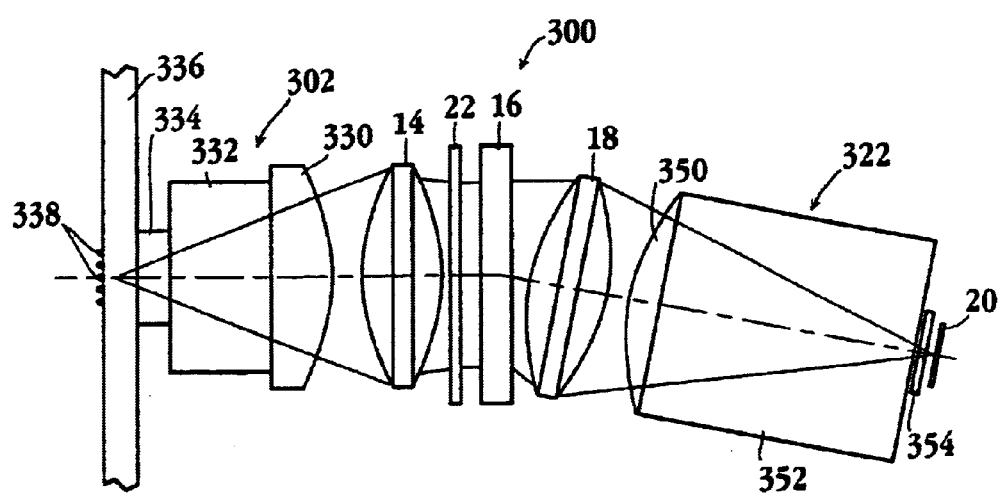
FIG. 28 is a side view of an embodiment of the optical system of FIG. 27.

The geometry of the hemispherical element 302 is shown schematically as a single element in FIG. 27. The hemispherical element may also be composed of several different elements as shown in FIG. 28. In FIG. 28, the hemispherical element 302 is composed of several different elements, such as a curved member 330 and rectangular optical elements 332, 334, and 336. In the embodiment of FIG. 28, the rectangular element 336 may be a slide or other sample holder. The samples 338 are preferably positioned at the object plane from the collection lens 14. Each of the elements 330, 332, 334, and 336 preferably have a uniform index of refraction.

As shown in FIG. 28, the optical system further includes a blocking filter 22 as discussed previously. Alternately, an aperture may be positioned at the location of the blocking filter 22. The optical system further includes a light dispersing element 16, such as a transmission grating, and a reimaging lens 18. The second hemispherical element 322 may also include a plurality of elements, such as curved member 350 and rectangular optical element 352. The second hemispherical element is sized so that the radius of curvature is slightly less than the space provided between the reimaging lens 18 and the light detection device at or near object plane 20. If a light detection window 354 is provided as shown in FIG. 28, the second hemispherical element 322 will be designed to fill substantially all of the space between the reimaging lens 18 and the light detection window 354 of the light detection device.

Figure 29:
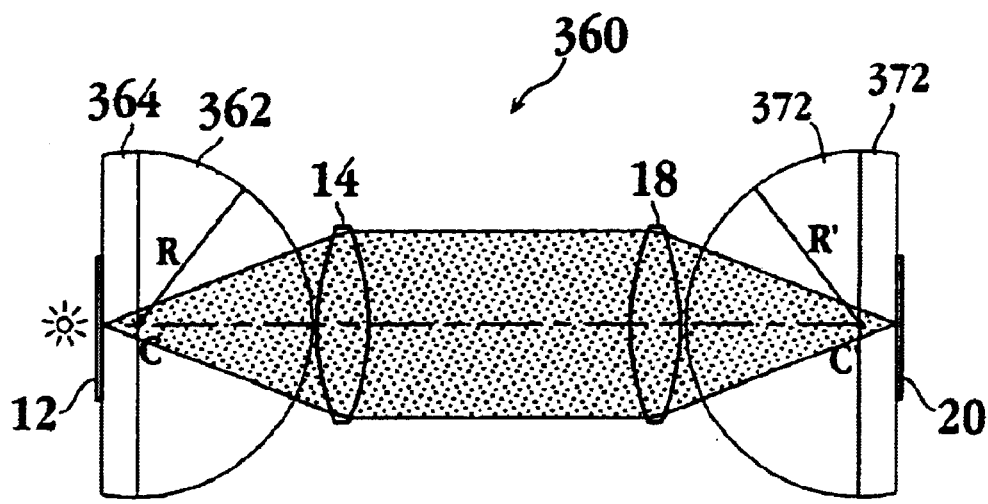
FIG. 29 is a schematic of another optical system with a hemispherical element.

According to other embodiments of the present invention, the hemispherical element may be configured so that it slightly magnifies the image of the sample. This is shown for example in optical system 360 of FIG. 29, where a hemispherical element 362 has a center of curvature C spaced from the object plane 12. The radius of curvature R in FIG. 29 is smaller than the radius of curvature described in FIG. 27. As shown in FIG. 29, the hemispherical element 362 may include an additional optical element 364 so that a significant gap does not exist between a flat surface of the hemispherical element and the object plane 12. The second hemispherical element 372 may have a radius of curvature R' less than the distance between the reimaging lens 18 and the image plane 20, for purposes similar to those described for the first hemispherical element 362. The second hemispherical element may also include one or more additional optical elements 374.

Various other embodiments exist for use with a hemispherical element. For example, it may be desirable to have some of the elements of a hemispherical element made from elements with different indexes of refraction. This may be particular suitable in optical systems in which aberration is a problem. In such a design, an element having a higher or lower index of refraction than the other elements may be inserted at any suitable location inside the hemispherical element. In other embodiments, curved surfaces may be provided inside of the hemispherical element.

The hemispherical element may be configured to be other shapes than perfectly hemispherical. For example, the hemispherical element may be slightly non-hemispherical or aspheric. Other suitable alternate geometries may also be acceptable with the present invention.

Methods of optically analyzing light from a sample are apparent from the description of the various embodiments of the optical system above. The methods include providing at least one sample holder having a sample therein. One example of suitable sample holders are the separation capillaries 202 shown in FIG. 2. As previously discussed, a variety of other types of sample holders are also acceptable. The method further includes illuminating the sample with an excitation light to generate an emission light. The sample, or plurality of samples, may be illuminated by a variety of different excitation sources such as lasers, as previously discussed. One or several of such excitation sources may be provided. The samples in the sample holders are caused to fluoresce by the excitation source so that they emit an emission light.

The emitted light from the sample holders is then collected by a collection lens (or first lens unit) that substantially collimates the light. The collimated light is directed toward a light dispersing element, such as a transmission grating, which spectrally disperses the substantially collimated light. Each of the various wavelengths is dispersed at a distinct angle by the light dispersing element. The dispersed and collimated light from the light dispersing element is then directed onto a light detection device by a reimaging lens (or second lens unit). The light detection device is preferably located substantially at the image plane of the reimaging lens. The light detection device, for example, a two-dimensional multi-element planar detector with a plurality of detection elements, detects the spectral characteristics of the emission light. The spectral characteristics may then be analyzed by any means such as a computer.

The method may also comprise other procedures such as blocking a significant portion of light having a wavelength lower than a predetermined wavelength using an interference filter. Moreover, to compensate for possible chromatic aberration, the light detection device or other elements may be tilted with respect to the optical axis of the collection lens so that light is focused on a plane of the light detection device. Alternately, or in addition to tilting the light detection device, at least one of the reimaging lens 18 and transmission grating 16 may be tilted with respect to the optical axis of the collection lens so that light is focused on a plane of the light detection device. The method may also include selectively blocking the light between the collection lens and the reimaging lens with a football shaped aperture. The method may further include positioning a correction lens between the collection lens and the reimaging lens to reduce curvature of the image on the light detection device. Other methods suitable with the optical system described above may also be used.

It will be apparent to those skilled in the art that various modifications and variations can be made in the optical systems, methods of optically analyzing light from a sample, use of the apparatus of the present invention, and in construction of this apparatus, without departing from the scope or spirit of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. All documents cited herein are incorporated by reference for any purpose.

What is claimed is:

1. An optical system for analyzing light from a plurality of samples, comprising:
   a plurality of sample holders;
   a collection lens configured to receive and substantially collimate light from the plurality of sample holders;
   a substantially hemispherical optical element comprising a flat surface facing the plurality of sample holders, a hemispherically curved surface facing said collection lens, and a radius of curvature, the center of said radius of curvature being located substantially on an optical axis of the collection lens and substantially at or near an object plane of the collection lens;
   a transmission grating configured to spectrally disperse the substantially collimated light from the collection lens; and
   a reimaging lens configured to receive the spectrally dispersed light from the transmission grating and direct the spectrally dispersed light onto a light detection device.

2. The system of claim 1 wherein the system further comprises said light detection device, and wherein said light detection device is a two-dimensional, multi-element photodetector having respectively perpendicular spatial and spectral detection axes.

3. The system of claim 2, wherein light from the plurality of sample holders is spatially dispersed along the spatial detection axis of the photodetector, such that light from each sample holder can be detected.

4. The system of claim 2 wherein light from each sample holder is spectrally dispersed along the spectral detection axis of the photodetector, such that a plurality of spectral components of the light from each sample holder can be detected.

5. The system of claim 3 wherein the system is configured to independently detect light from each sample holder.

6. The system of claim 4 wherein the system is configured to independently detect the plurality of spectral components.

7. The system of claim 2 wherein said system is configured to compensate for chromatic aberration in the spectrally dispersed light, the compensation comprising an optical axis of the reimaging lens being non-perpendicular with a surface of the photodetector.

8. The system of claim 7, wherein a plurality of spectral components are focused onto a plane of the photodetector.

9. The system of claim 1 wherein the radius of curvature of the hemispherical optical element is approximately equal to a distance between the collection lens and the sample.

10. The system of claim 1, wherein the hemispherical optical element comprises at least one optical element.

11. The system of claim 1 wherein the hemispherical optical element comprises more than one optical element.

12. The system of claim 1, wherein the hemispherical optical element comprises at least one rectangular element.

13. The system of claim 1 wherein the hemispherical optical element is configured to magnify the light from the plurality of sample holders.

14. The system of claim 1 wherein the hemispherical optical element is aspheric.

15. The system of claim 1, wherein the system further comprises the light detection device and a second substantially hemispherical optical element located between the reimaging lens and the light detection device, wherein the second substantially hemispherical optical element comprises a flat surface facing the light detection device, a hemispherically curved surface facing the reimaging lens, and a radius of curvature, the center of said radius of curvature being located substantially on an optical axis of the reimaging lens and substantially at or near an object plane of the reimaging lens.

16. The system of claim 1 further comprising an excitation light source for illuminating the plurality of sample holders.

17. The system of claim 16 wherein light from the excitation light source does not pass through the collection lens prior to illuminating the sample holders.

18. The system of claim 1, wherein said system comprises not more than one transmission grating.

19. The system of claim 1 wherein the plurality of sample holders comprise electrophoresis lanes.

20. The system of claim 19, wherein at least one of said lanes is located in a capillary.

21. The system of claim 1, further comprising an optical filter positioned at least one of between the plurality of sample holders and the collection lens and between the collection lens and the reimaging lens.

22. The system of claim 21, wherein said optical filter is an interference filter.

23. The system of claim 21, wherein said optical filter substantially blocks light.

24. The system of claim 21, wherein said optical filter substantially blocks light having a wavelength shorter than an excitation wavelength of the plurality of samples.

25. The system of claim 21, wherein said optical filter substantially blocks light having a wavelength substantially equal to an excitation wavelength of the plurality of samples.

26. The system of claim 1, wherein the system further comprises the light detection device, and wherein the light detection device is located at the image plane of the reimaging lens.

27. The system of claim 1, wherein the system further comprises the light detection device, and wherein the light detection device comprises a charge-coupled device (CCD).

28. The system of claim 1, wherein the system further comprises the light detection device, and wherein the light detection device includes an anti-reflective coating.

29. The system of claim 1, further comprising an aperture positioned between the collection lens and the reimaging lens.

30. The system of claim 29 wherein the aperture is configured to provide substantially uniform light throughput.

31. The system of claim 29 wherein the aperture is in the shape of a cat's eye.

32. The system of claim 1 wherein the system further comprises the light detection device and a correction lens positioned between the collection lens and the reimaging lens, and configured to reduce a curvature of the image on the light detection device.

33. An optical system for analyzing light from a plurality of samples, comprising:
   a plurality of sample holders;
   a collection lens configured to receive and substantially collimate light from the plurality of sample holders;
   a substantially hemispherical optical element comprising a flat surface facing the plurality of sample holders, a hemispherically curved surface facing said collection lens, and a radius of curvature, the center of said radius of curvature being located substantially on an optical axis of the collection lens and substantially at or near an object plane of the collection lens;

a transmission grating configured to spectrally disperse the substantially collimated light from the collection lens; and a reimaging lens configured to receive the spectrally dispersed light from the transmission grating and direct the light onto a light detection device, wherein said system is configured to compensate for chromatic aberration in the spectrally dispersed light, the compensation comprising an optical axis of the reimaging lens being non-perpendicular with a surface of the light detection device.

34. The system of claim 33, wherein the system further comprises the light detection device, and wherein said light detection device is a two-dimensional, multi-element photodetector having respectively perpendicular spatial and spectral detection axes.

35. The system of claim 34 wherein light from the plurality of sample holders is spatially dispersed along the spatial detection axis of the photodetector, such that light from each sample holder can be detected.

36. The system of claim 35 wherein light from each sample holder is spectrally dispersed along the spectral detection axis of the photodetector, such that a plurality of spectral components of the light from each sample holder can be detected.

37. The system of claim 36, wherein the system is configured to independently detect light from each sample holder.

38. The system of claim 37, wherein the system is configured to independently detect the plurality of spectral components.

39. The system of claim 33 wherein the system further comprises the light detection device, and wherein a plurality of spectral components are focused onto a plane of the light detection device.

40. The system of claim 33, wherein the radius of curvature of the hemispherical optical element is approximately equal to a distance between the collection lens and the sample.

41. The system of claim 33, wherein the hemispherical optical element comprises at least one optical element.

42. The system of claim 33 wherein the hemispherical optical element comprises more than one optical element.

43. The system of claim 33 wherein the hemispherical optical element comprises at least one rectangular element.

44. The system of claim 33, wherein the hemispherical optical element is configured to magnify the light from the plurality of sample holders.

45. The system of claim 33 wherein the hemispherical optical element is aspheric.

46. The system of claim 33 wherein the system further comprises the light detection device and a second substantially hemispherical optical element located between the reimaging lens and the light detection device, wherein the second substantially hemispherical optical element comprises a flat surface facing the light detection device, a hemispherically curved surface facing the reimaging lens, and a radius of curvature, the center of said radius of curvature being located substantially on an optical axis of the reimaging lens and substantially at or near an object plane of the reimaging lens.

47. The system of claim 33, further comprising an excitation light source for illuminating the plurality of sample holders.

48. The system of claim 47 wherein light from the excitation light source does not pass through the collection lens prior to illuminating the plurality of sample holders.

49. The system of claim 33 wherein said system comprises not more than one transmission grating.

50. The system of claim 33, wherein the plurality of sample holders comprise electrophoresis lanes.

51. The system of claim 50 wherein at least one of said lanes is located in a capillary.

52. The system of claim 33, further comprising an optical filter positioned at least one of between the plurality of sample holders and the collection lens and between the collection lens and the reimaging lens.

53. The system of claim 52, wherein said optical filter is an interference filter.

54. The system of claim 52, wherein said optical filter substantially blocks light.

55. The system of claim 52, wherein said optical filter substantially blocks light having a wavelength shorter than an excitation wavelength of the plurality of samples.

56. The system of claim 52 wherein said optical filter substantially blocks light having a wavelength substantially equal to an excitation wavelength wavelength of the plurality of samples.

57. The system of claim 33 wherein the system further comprises the light detection device, and wherein the light detection device is located at the image plane of the reimaging lens.

58. The system of claim 33, wherein the system further comprises the light detection device, and wherein the light detection device comprises a charge-coupled device (CCD).

59. The system of claim 33, wherein the system further comprises the light detection device, and wherein the light detection device includes an anti-reflective coating.

60. The system of claim 33, further comprising an aperture positioned between the collection lens and the reimaging lens.

61. The system of claim 60, wherein the aperture is configured to provide substantially uniform light throughput.

62. The system of claim 61 wherein the aperture is in the shape of a cat's eye.

63. The system of claim 33, wherein the system further comprises the light detection device and a correction lens positioned between the collection lens and the reimaging lens to reduce the curvature of the image on the light detection device.

64. The system of claim 33, wherein the system further comprises the light detection device, and wherein the spectrally dispersed light is focused onto a plane of the light detection device.

65. An optical system for analyzing light from a plurality of samples, comprising:

a plurality of sample holders;

a collection lens configured to receive and substantially collimate light from the plurality of sample holders;

a transmission grating configured to spectrally disperse the substantially collimated light from the collection lens; and a reimaging lens configured to receive the spectrally dispersed light from the transmission grating and direct the light onto a light detection device, wherein said system is configured to compensate for chromatic aberration in the spectrally dispersed light, the compensation comprising an optical axis of the reimaging lens being non-perpendicular with a surface of the light detection device.

66. The system of claim 65, further comprising a substantially hemispherical optical element comprising a flat surface facing the plurality of sample holders, a hemispherically curved surface facing said collection lens, and a radius of curvature, the center of said radius of curvature being located substantially on an optical axis of the collection lens and substantially at or near an object plane of the collection lens.

67. The system of claim 66, wherein the radius of curvature of the hemispherical optical element is approximately equal to a distance between the collection lens and the sample.

68. The system of claim 66 wherein the hemispherical optical element comprises at least one optical element.

69. The system of claim 66, wherein the hemispherical optical element comprises more than one optical element.

70. The system of claim 66 wherein the hemispherical optical element comprises at least one rectangular element.

71. The system of claim 66 wherein the hemispherical optical element is configured to magnify the light from the plurality of sample holders.

72. The system of claim 66, wherein the hemispherical optical element is aspheric.

73. The system of claim 65, wherein the system further comprises the light detection device and a second substantially hemispherical optical element located between the reimaging lens and the light detection device, wherein the second substantially hemispherical optical element comprises a flat surface facing the light detection device, a hemispherically curved surface facing the reimaging lens, and a radius of curvature, the center of said radius of curvature being located substantially on an optical axis of the reimaging lens and substantially at or near an object plane of the reimaging lens.

74. The optical system of claim 65, further comprising an excitation light source for illuminating the plurality of sample holders.

75. The optical system of claim 74, wherein light from the excitation light source does not pass through the collection lens prior to illuminating the sample holders.

76. The optical system of claim 65, wherein said system comprises not more than one transmission grating.

77. The optical system of claim 65, wherein the plurality of sample holders comprise electrophoresis lanes.

78. The optical system of claim 77 wherein at least one of said lanes is located in a capillary.

79. The optical system of claim 65, further comprising an optical filter positioned at least one of between the plurality of sample holders and the collection lens and between the collection lens and the reimaging lens.

80. The optical system of claim 79, wherein said optical filter is an interference filter.

81. The optical system of claim 79, wherein said optical filter substantially blocks light.

82. The optical system of claim 79 wherein said optical filter substantially blocks light having a wavelength shorter than an excitation wavelength of the plurality of samples.

83. The optical system of claim 79, wherein said optical filter substantially blocks light having a wavelength substantially equal to the excitation wavelength of the plurality of samples.

84. The optical system of claim 65, wherein the system further comprises the light detection device, and wherein the light detection device is located at the image plane of the reimaging lens.

85. The optical system of claim 65, wherein the system further comprises the light detection device, and wherein the light detection device comprises a charge-coupled device (CCD).

86. The optical system of claim 65, wherein the system further comprises the light detection device, and wherein the light detection device includes an anti-reflective coating.

87. The optical system of claim 65, further comprising an aperture positioned between the collection lens and the reimaging lens.

88. The optical system of claim 87, wherein the aperture is configured to provide substantially uniform light throughput.

89. The optical system of claim 88, wherein the aperture is in the shape of a cat's eye.

90. The optical system of claim 65, wherein the system further comprises the light detection device and a correction lens positioned between the collection lens and the reimaging lens, and configured to reduce the curvature of the image on the light detection device.

91. A system for analyzing light from a sample in a separation system, comprising:
   at least one separation lane;
   a collection lens configured to receive and substantially collimate light emitted from the at least one separation lane;
   a substantially hemispherical optical element comprising a flat surface facing the at least one separation lane, a hemispherically curved surface facing said collection lens, and a radius of curvature, the center of said radius of curvature being located substantially on an optical axis of the collection lens and substantially at or near an object plane of the collection lens;
   a light dispersing element configured to spectrally disperse substantially collimated light from the collection lens; and
   a reimaging lens configured to receive light from the light dispersing element and direct the light onto a light detection device,
   wherein said system is configured to compensate for chromatic aberration in the spectrally dispersed light, the compensation comprising an optical axis of the reimaging lens being non-perpendicular with a surface of the light detection device.

92. The system of claim 91, wherein the at least one separation lane comprises a plurality of separation lanes.

93. The system of claim 92, wherein the plurality of separation lanes comprise separation capillaries positioned in a planar array.

94. The system of claim 91, wherein the at least one separation lane comprises only a single separation lane.

95. The system of claim 91, wherein said light dispersing element comprises a transmission grating.

96. The system of claim 91 wherein said light dispersing element comprises a reflection grating.

97. The system of claim 91, wherein the system further comprises the light detection device, and wherein the light detection device is a multi-element photodetector configured to analyze light from the plurality of separation lanes.

98. The system of claim 97 wherein the multi-element photodetector comprises a charge-coupled device (CCD).

99. The system of claim 91, wherein the system further comprises the light detection device, and wherein the light detection device is located at substantially the image plane of the reimaging lens.

100. The system of claim 91 further comprising a light source providing an excitation light to the at least one separation lane.

101. The system of claim 91 wherein the radius of curvature of the hemispherical optical element is approximately equal to a distance between the collection lens and the sample.

102. The system of claim 91, wherein the hemispherical optical element comprises at least one optical element.

103. The system of claim 91, wherein the hemispherical optical element comprises more than one optical element.

104. The system of claim 91, wherein the hemispherical optical element comprises at least one rectangular element.

105. The system of claim 91, wherein the hemispherical optical element is configured to magnify the light from at least one separation lane.

106. The system of claim 91, wherein the hemispherical optical element is aspheric.

107. The system of claim 91, wherein the system further comprises the light detection device and a second substantially hemispherical optical element located between the reimaging lens and the light detection device, wherein the second substantially hemispherical optical element comprises a flat surface facing the light detection device, a hemispherically curved surface facing the reimaging lens, and a radius of curvature, the center of said radius of curvature being located substantially on an optical axis of the reimaging lens and substantially at or near an object plane of the reimaging lens.

108. A system for analyzing light from a light source, comprising:
    a collection lens configured to receive and substantially collimate light emitted from the light source;
    a substantially hemispherical optical element comprising a flat surface facing the light source, a hemispherically curved surface facing said collection lens, and a radius of curvature, the center of said radius of curvature being located substantially on an optical axis of the collection lens and substantially at or near an object plane of the collection lens;
    a light dispersing element configured to spectrally disperse the substantially collimated light from the collection lens; and
    a reimaging lens configured to receive the spectrally dispersed light from the light dispersing element and direct the light onto a light detection device,
    wherein said system is configured to compensate for chromatic aberration in the spectrally dispersed light, the compensation comprising an optical axis of the reimaging lens being non-perpendicular with a surface of the light detection device.

109. The system of claim 108, wherein the system comprises at least one separation lane.

110. The system of claim 109, wherein said at least one separation lane comprises said light source.

111. The system of claim 109, wherein the at least one separation lane comprises a plurality of separation lanes.

112. The system of claim 111, wherein the plurality of separation lanes comprise separation capillaries positioned in an planar array.

113. The system of claim 109 wherein the at least one separation lane comprises only a single separation lane.

114. The system of claim 108 wherein said light dispersing element comprises a transmission grating.

115. The system of claim 108, wherein said light dispersing element comprises a reflection grating.

116. The system of claim 111, wherein the system further comprises the light detection device, and wherein the light detection device is a multi-element photodetector configured to analyze light from the plurality of separation lanes.

117. The system of claim 116, wherein the multi-element photodetector comprises a charge-coupled device (CCD).

118. The system of claim 108 wherein the system further comprises the light detection device, and wherein the light detection device is located at substantially the image plane of the reimaging lens.

119. The system of claim 110 further comprising an excitation light source providing an excitation light to the at least one separation lane.

120. The system of claim 108 wherein the radius of curvature of the hemispherical optical element is approximately equal to a distance between the collection lens and the sample.

121. The system of claim 108, wherein the hemispherical optical element comprises at least one optical element.

122. The system of claim 108, wherein the hemispherical optical element comprises more than one optical element.

123. The system of claim 108 wherein the hemispherical optical element comprises at least one rectangular element.

124. The system of claim 108, wherein the hemispherical optical element is configured to magnify the light from the light source.

125. The system of claim 108, wherein the hemispherical optical element is aspheric.

126. A system for analyzing light from a sample in a separation system, comprising:
    at least one separation lane;
    a collection lens configured to receive and substantially collimate light emitted from the at least one separation lane;
    a substantially hemispherical optical element comprising a flat surface facing the at least one separation lane, a hemispherically curved surface facing said collection lens, and a radius of curvature, the center of said radius of curvature being located substantially on an optical axis of the collection lens and substantially at or near an object plane of the collection lens;
    a transmission grating configured to spectrally disperse the substantially collimated light from the collection lens; and
    a reimaging lens configured to receive the spectrally dispersed light from the transmission grating and direct the spectrally dispersed light onto a light detection device,
    wherein said system is configured to compensate for chromatic aberration in the spectrally dispersed light, the compensation comprising an optical axis of the reimaging lens being non-perpendicular with a surface of the light detection device.

127. The system of claim 126 wherein the at least one separation lane comprises a plurality of separation lanes.

128. The system of claim 127 wherein the separation lanes comprise separation capillaries positioned in an planar array.

129. The system of claim 126, wherein the at least one separation lane comprises only a single separation lane.

130. The system of claim 127, wherein the system further comprises the light detection device, and wherein the light detection device is a multi-element photodetector configured to analyze light from the plurality of separation lanes.

131. The system of claim 130, wherein the multi-element photodetector comprises a charge-coupled device (CCD).

132. The system of claim 126, wherein the system further comprises the light detection device, and wherein the light detection device is located at substantially the image plane of the reimaging lens.

133. The system of claim 126 further comprising a light source providing an excitation light to the at least one separation lane.

134. The system of claim 126 wherein the radius of curvature of the hemispherical optical element is approximately equal to a distance between the collection lens and the sample.

135. The system of claim 126 wherein the hemispherical optical element comprises at least one optical element.

136. The system of claim 126 wherein the hemispherical optical element comprises more than one optical element.

137. The system of claim 126 wherein the hemispherical optical element comprises at least one rectangular element.

138. The system of claim 126 wherein the hemispherical optical element is configured to magnify the light from the at least one separation lane.

139. The system of claim 126, wherein the hemispherical optical element is aspheric.

140. The system of claim 126, wherein the system further comprises the light detection device and a second substantially hemispherical optical element located between the reimaging lens and the light detection device, wherein the second substantially hemispherical optical element comprises a flat surface facing the light detection device, a hemispherically curved surface facing the reimaging lens, and a radius of curvature, the center of said radius of curvature being located substantially on an optical axis of the reimaging lens and substantially at or near an object plane of the reimaging lens.

141. A method of optically analyzing a plurality of samples, comprising:
providing a plurality of samples;
illuminating the samples with an excitation light to generate an emission light;
collecting the emission light emitted from the samples with a collection lens, said collecting comprising collecting the emission light through a substantially hemispherical element located between the collection lens and the plurality of samples, wherein the substantially hemispherical optical element comprises a flat surface facing the plurality of samples, a hemispherically curved surface facing said collection lens, and a radius of curvature, the center of said radius of curvature being located substantially on an optical axis of the collection lens and substantially at or near an object plane of the collection lens;
substantially collimating the emission light with the collection lens;
spectrally dispersing the substantially collimated emission light with a transmission grating;
directing the spectrally dispersed emission light from the transmission grating onto a light detection device by a reimaging lens; and
optically detecting the spectral characteristics of the spectrally dispersed emission light with a light detection device, wherein
said excitation light does not pass through the collection lens prior to illuminating the sample; and
further comprising compensating for chromatic aberration in the spectrally dispersed emission light, the compensating comprising configuring an optical axis of the reimaging lens to be non-perpendicular with a surface of the light detection device.

142. The method of claim 141, wherein said light detection device is a two-dimensional, multi-element photodetector having respectively perpendicular spatial and spectral detection axes.

143. The method of claim 142, wherein the spectrally dispersed emission light is spatially dispersed along the spatial detection axis of the photodetector, such that light from each sample holder can be independently detected.

144. The method of claim 142, wherein the spectrally dispersed emission light is spectrally dispersed along the spectral detection axis of the photodetector, such that a plurality of spectral components of the light from each sample can be independently detected.

145. The method of claim 141 wherein the providing the plurality of samples includes providing the plurality of samples to a plurality of separation lanes.

146. The method of claim 145 wherein the plurality of separation lanes comprise capillaries for electrophoresis.

147. The method of claim 144, further comprising blocking a portion of light of a predetermined wavelength or range of wavelengths using an optical filter.

148. The method of claim 147 wherein the optical filter comprises an interference filter.

149. The method of claim 144 further comprising selectively blocking the light between the collection lens and the reimaging lens with an aperture.

150. The method of claim 149 wherein said selective blocking of the light provides for substantially uniform light throughput.

151. The method of claim 150 wherein said aperture is in the shape of a cat's eye.

152. The method of claim 141 further comprising coating the light detection device with an anti-reflective material.

153. The method of claim 141, further comprising positioning a correction lens between the collection lens and the reimaging lens to reduce curvature of the image on the light detection device.

154. The method of claim 153 further comprising placing a second substantially hemispherical element between the reimaging lens and the image plane of the reimaging lens.

155. A method of optically analyzing a plurality of samples, comprising:
providing a plurality of samples;
illuminating the plurality of samples with an excitation light to generate an emission light;
collecting the emission light emitted from the plurality of samples with a collection lens, said collecting comprising collecting the emission light through a substantially hemispherical element located between the collection lens and the plurality of samples, wherein the substantially hemispherical optical element comprises a flat surface facing the plurality of samples, a hemispherically curved surface facing said collection lens, and a radius of curvature, the center of said radius of curvature being located substantially on an optical axis of the collection lens and substantially at or near an object plane of the collection lens;
substantially collimating the emission light with the collection lens;
spectrally dispersing the substantially collimated emission light with a transmission grating;
directing the spectrally dispersed emission light from the transmission grating onto a light detection device by a reimaging lens; and
optically detecting spectral characteristics of the spectrally dispersed emission light,
wherein said excitation light does not pass through the collection lens prior to illuminating the sample.

156. The method of claim 155, wherein said light detection device is a two-dimensional, multi-element photodetector having respectively perpendicular spatial and spectral detection axes.

157. The method of claim 156, wherein the spectrally dispersed emission light is spatially dispersed along the spatial detection axis of the photodetector, such that light from each sample holder can be independently detected.

158. The method of claim 156 wherein the spectrally dispersed emission light is spectrally dispersed along the spectral detection axis of the photodetector, such that a plurality of spectral components of the light from each sample holder can be independently detected.

159. The method of claim 155, wherein the providing the plurality samples includes providing the plurality of samples to a plurality of separation lanes.

160. The method of claim 159, wherein the plurality of separation lanes comprise capillaries for electrophoresis.

161. The method of claim 155 further comprising blocking a portion of light of a predetermined wavelength or range of wavelengths using an optical filter.

162. The method of claim 161, wherein the optical filter comprises an interference filter.

163. The method of claim 155, further comprising tilting the light detection device with respect to the optical axis of the reimaging lens so that the light is focused on a plane of the light detection device.

164. The method of claim 155 further comprising selectively blocking the light between the collection lens and the reimaging lens with an aperture.

165. The method of claim 164, wherein said selective blocking of the light provides for substantially uniform light throughput.

166. The method of claim 165 wherein said aperture is in the shape of a cat's eye.

167. The method of claim 155, further comprising coating the light detection device with an anti-reflective material.

168. The method of claim 155, further comprising positioning a correction lens between the collection lens and the reimaging lens to reduce curvature of the image on the light detection device.

169. The method of claim 155, further comprising placing a second substantially hemispherical element between the reimaging lens and the image plane of the reimaging lens.

170. A method of optically analyzing a plurality of samples, comprising:
providing a plurality of samples;
illuminating the plurality of samples with an excitation light to generate an emission light;
collecting the emission light emitted from the sample with a collection lens;
substantially collimating the emission light with the collection lens;
spectrally dispersing the substantially collimated emission light with a transmission grating;
directing the spectrally dispersed emission light from the transmission grating onto a light detection device by a reimaging lens; and
optically detecting spectral characteristics of the spectrally dispersed emission light,
wherein said excitation light does not pass through the collection lens prior to illuminating the sample; and
further comprising compensating for chromatic aberration in the spectrally dispersed emission light, the compensating comprising configuring an optical axis of the reimaging lens to be non-perpendicular with a surface of the light detection device.

171. The method of claim 170 wherein said light detection device is a two-dimensional, multi-element photodetector having respectively perpendicular spatial and spectral detection axes.

172. The method of claim 170, wherein the spectrally dispersed emission light is spatially dispersed along the spatial detection axis of the photodetector, such that light from each sample holder can be independently detected.

173. The method of claim 170 wherein the spectrally dispersed emission light is spectrally dispersed along the spectral detection axis of the photodetector, such that a plurality of spectral components of the light from each sample can be independently detected.

174. The method of claim 170 wherein the providing the plurality of samples includes providing the plurality of samples to a plurality of separation lanes.

175. The method of claim 174 wherein the plurality of separation lanes comprise capillaries for electrophoresis.

176. The method of claim 170 further comprising, blocking a portion of light of a predetermined wavelength or range of wavelengths using an optical filter.

177. The method of claim 176, wherein the optical filter comprises an interference filter.

178. The method of claim 170, further comprising selectively blocking the light between the collection lens and the reimaging lens with an aperture.

179. The method of claim 178, wherein said selective blocking of the light provides for substantially uniform light throughput.

180. The method of claim 178, wherein said aperture is in the shape of a cat's eye.

181. The method of claim 170, further comprising coating the light detection device with an anti-reflective material.

182. The method of claim 170 further comprising positioning a correction lens between the collection lens and the reimaging lens to reduce curvature of the image on the light detection device.

183. The method of claim 170, further comprising placing a substantially hemispherical element at least one of between the collection lens and the object plane of the collection lens, and the reimaging lens and between the image plane of the reimaging lens.

184. An optical system for analyzing light from a plurality of samples, comprising:
a plurality of sample holders;
a collection lens configured to receive and substantially collimate light from the plurality of sample holders;
an optical element comprising at least a hemispherical portion having a diametral plane and a curved surface facing the collection lens, a flat surface facing the plurality of sample holders, and a radius of curvature, the center of said radius of curvature being located substantially on an optical axis of the collection lens and substantially at or near an object plane of the collection lens;
a transmission grating configured to spectrally disperse the substantially collimated light from the collection lens; and
a reimaging lens configured to receive the spectrally dispersed light from the transmission grating and direct the spectrally dispersed light onto a light detection device.

185. The system of claim 184 wherein the optical element is extended perpendicular to the diametral plane in a direction away from the curved surface.

186. The system of claim 185, wherein the extension has a substantially constant width parallel to the diametral plane.

187. The system of claim 185, wherein the extension has more than one width parallel to the diametral plane.

188. The system of claim 256, wherein the more than one width comprises widths that decrease along the extension in the direction away from the curved surface.

189. The system of claim 185 wherein the optical element comprises one optical element.

190. The system of claim 185 wherein the optical element comprises more than one optical element.

191. The system of claim 184, wherein the curved surface is a substantially hemispherically curved surface.

* * * * *